(12) United States Patent
Ivri

(10) Patent No.: US 10,583,038 B2
(45) Date of Patent: Mar. 10, 2020

(54) PIEZOELECTRIC DISPENSER WITH REPLACEABLE AMPOULE

(71) Applicant: Kedalion Therapeutics, Inc., Menlo Park, CA (US)

(72) Inventor: Yehuda Ivri, Newport Beach, CA (US)

(73) Assignee: Kedalion Therapeutics, Menlo Park, CA (US)

( * ) Notice: Subject to any disclaimer, the term of this patent is extended or adjusted under 35 U.S.C. 154(b) by 246 days.

(21) Appl. No.: 15/094,849

(22) Filed: Apr. 8, 2016

(65) Prior Publication Data

US 2016/0296367 A1   Oct. 13, 2016

Related U.S. Application Data

(60) Provisional application No. 62/178,464, filed on Apr. 10, 2015.

(51) Int. Cl.
*A61F 9/00* (2006.01)
*A61M 15/00* (2006.01)
*A61M 11/00* (2006.01)

(52) U.S. Cl.
CPC .......... *A61F 9/0008* (2013.01); *A61F 9/0026* (2013.01); *A61M 11/005* (2013.01); *A61M 15/0028* (2013.01); *A61M 15/0043* (2014.02)

(58) Field of Classification Search
None
See application file for complete search history.

(56) References Cited

U.S. PATENT DOCUMENTS

| | | |
|---|---|---|
| 3,640,274 A | 2/1972 | Costello |
| 3,779,245 A | 12/1973 | Windsor |
| 3,812,854 A | 5/1974 | Michaels et al. |
| 3,976,072 A | 8/1976 | Walker |
| 4,159,803 A | 7/1979 | Cameto et al. |
| 4,300,546 A | 11/1981 | Kruber |

(Continued)

FOREIGN PATENT DOCUMENTS

| | | |
|---|---|---|
| CN | 104146816 A | 11/2014 |
| EP | 622035 A1 | 11/1994 |

(Continued)

OTHER PUBLICATIONS

Murube, J. et al., "Classification of artificial tears: I. Composition and properties," *Adv Exp Med Biol.*, 438:693-704, 49, 1998.

(Continued)

*Primary Examiner* — Bhisma Mehta
*Assistant Examiner* — Matthew A Engel
(74) *Attorney, Agent, or Firm* — Lumen Patent Firm

(57) ABSTRACT

Fluid delivery devices and methods are described where the device may comprise a piezoelectric actuator having a piezoelectric chip that is operatively coupled to a drug package under a preloading force. The actuator is configured to generate an acoustic pressure within the drug package to dispense droplets or a continuous stream of an agent from an aperture, e.g., to the corneal surface of the eye. The piezoelectric actuator can be coupled or decoupled from the drug package via a coupling mechanism which enables the quick release and consistent securement of the drug package to the actuator and housing.

8 Claims, 15 Drawing Sheets

(56) References Cited

U.S. PATENT DOCUMENTS

| | | | |
|---|---|---|---|
| 4,334,531 A | 6/1982 | Reichl et al. | |
| 4,338,576 A | 7/1982 | Takahashi et al. | |
| 4,352,459 A | 10/1982 | Berger et al. | |
| 4,465,234 A | 8/1984 | Maehara et al. | |
| 4,632,311 A | 12/1986 | Nakane et al. | |
| 4,655,393 A | 4/1987 | Berger | |
| 4,850,534 A | 7/1989 | Takahashi et al. | |
| 4,882,150 A | 11/1989 | Kaufman | |
| 4,961,345 A | 10/1990 | Tsuruoka et al. | |
| 4,981,625 A * | 1/1991 | Rhim | A61K 9/1635 |
| | | | 264/10 |
| 5,171,306 A | 12/1992 | Vo | |
| 5,232,363 A | 8/1993 | Meller | |
| 5,368,582 A | 11/1994 | Bertera | |
| 5,487,378 A | 1/1996 | Robertson et al. | |
| 5,624,057 A | 4/1997 | Lifshey | |
| 5,630,793 A | 5/1997 | Rowe | |
| 5,657,926 A | 8/1997 | Toda | |
| 5,938,117 A | 8/1999 | Ivri | |
| 6,062,212 A | 5/2000 | Davison et al. | |
| 6,273,092 B1 | 8/2001 | Nolan | |
| 6,467,476 B1 | 10/2002 | Ivri et al. | |
| RE38,077 E | 4/2003 | Cohen et al. | |
| 6,629,646 B1 | 10/2003 | Ivri | |
| 6,730,066 B1 | 5/2004 | Bennwik et al. | |
| 6,758,837 B2 | 7/2004 | Peclat et al. | |
| 7,066,398 B2 | 6/2006 | Borland et al. | |
| 7,201,732 B2 | 4/2007 | Anderson et al. | |
| 7,883,031 B2 | 2/2011 | Collins et al. | |
| 8,012,136 B2 | 9/2011 | Collins et al. | |
| 8,128,606 B2 | 3/2012 | Anderson et al. | |
| 8,133,210 B2 | 3/2012 | Al-Abdulla et al. | |
| 8,273,307 B2 | 9/2012 | Eickhoff et al. | |
| 8,398,001 B2 | 3/2013 | Borland et al. | |
| 8,435,544 B2 | 5/2013 | Mitra et al. | |
| 8,545,463 B2 | 10/2013 | Collins et al. | |
| 8,684,980 B2 | 4/2014 | Hunter et al. | |
| 8,733,935 B2 | 5/2014 | Ballou, Jr. et al. | |
| 8,722,728 B2 | 7/2014 | Tredwell | |
| 8,936,021 B2 | 1/2015 | Collins | |
| 9,039,666 B2 | 5/2015 | Voss et al. | |
| 9,068,566 B2 | 6/2015 | Ivri | |
| 9,087,145 B2 | 7/2015 | Ballou et al. | |
| 9,186,690 B2 | 11/2015 | Scanlon et al. | |
| 9,597,230 B2 | 3/2017 | Haffner et al. | |
| 9,700,686 B2 | 7/2017 | Gavini et al. | |
| 9,801,757 B2 | 10/2017 | Voss et al. | |
| 10,073,949 B2 | 9/2018 | Ballou, Jr. et al. | |
| 10,154,923 B2 | 12/2018 | Hunter et al. | |
| 10,174,017 B2 | 1/2019 | deLong et al. | |
| 2001/0036449 A1 | 11/2001 | Garst | |
| 2002/0124843 A1 | 9/2002 | Skiba et al. | |
| 2002/0158196 A1 | 10/2002 | Berggren et al. | |
| 2002/0161344 A1 | 10/2002 | Peclat et al. | |
| 2004/0039355 A1 | 2/2004 | Gonzalez et al. | |
| 2004/0138630 A1 | 7/2004 | Al-Abdulla et al. | |
| 2004/0204674 A1 | 10/2004 | Anderson et al. | |
| 2004/0215157 A1 | 10/2004 | Peclat et al. | |
| 2004/0256487 A1 | 12/2004 | Collins et al. | |
| 2005/0006417 A1 | 1/2005 | Nicol et al. | |
| 2005/0172962 A1 | 8/2005 | Gumaste et al. | |
| 2005/0240162 A1 | 10/2005 | Chen et al. | |
| 2005/0261641 A1 | 11/2005 | Warchol et al. | |
| 2006/0147313 A1 | 7/2006 | Zengerle et al. | |
| 2007/0088267 A1* | 4/2007 | Shekalim | A61M 5/145 |
| | | | 604/134 |
| 2007/0119969 A1* | 5/2007 | Collins, Jr. | A61M 11/005 |
| | | | 239/102.1 |
| 2008/0039807 A1 | 2/2008 | Pine | |
| 2008/0202514 A1 | 8/2008 | Kriksunov et al. | |
| 2008/0214940 A1 | 9/2008 | Benaron et al. | |
| 2008/0233053 A1 | 9/2008 | Gross et al. | |
| 2008/0247264 A1 | 10/2008 | Gabl et al. | |
| 2009/0060793 A1 | 3/2009 | Eickhoff et al. | |
| 2009/0114742 A1* | 5/2009 | Collins, Jr. | A61M 11/005 |
| | | | 239/338 |
| 2009/0134235 A1 | 5/2009 | Ivri | |
| 2009/0192443 A1 | 7/2009 | Collins, Jr. et al. | |
| 2009/0212127 A1 | 8/2009 | Reynolds et al. | |
| 2009/0212133 A1 | 8/2009 | Collins, Jr. et al. | |
| 2009/0223513 A1 | 9/2009 | Papania et al. | |
| 2010/0044460 A1* | 2/2010 | Sauzade | B05B 17/0646 |
| | | | 239/102.2 |
| 2010/0076388 A1 | 3/2010 | Cater | |
| 2010/0222752 A1* | 9/2010 | Collins, Jr. | A61M 11/005 |
| | | | 604/296 |
| 2010/0295420 A1 | 11/2010 | Wierach | |
| 2011/0074247 A1 | 3/2011 | Hohlfeld et al. | |
| 2011/0106025 A1 | 5/2011 | Hall et al. | |
| 2011/0284579 A1 | 11/2011 | Pardes et al. | |
| 2012/0017898 A1 | 1/2012 | Moller | |
| 2012/0062840 A1 | 3/2012 | Ballou, Jr. et al. | |
| 2012/0070467 A1 | 3/2012 | Ballou, Jr. et al. | |
| 2012/0143152 A1* | 6/2012 | Hunter | A61B 5/0059 |
| | | | 604/298 |
| 2012/0179122 A1 | 7/2012 | Eilat et al. | |
| 2012/0197219 A1 | 8/2012 | Scanlon et al. | |
| 2012/0304929 A1* | 12/2012 | Ivri | F04B 43/046 |
| | | | 118/712 |
| 2013/0017283 A1 | 1/2013 | Zemel et al. | |
| 2013/0345672 A1 | 2/2013 | Tanikawa et al. | |
| 2013/0118619 A1 | 5/2013 | Loth et al. | |
| 2013/0150812 A1* | 6/2013 | Hunter | A61F 9/0008 |
| | | | 604/295 |
| 2013/0152796 A1 | 6/2013 | Pawl | |
| 2013/0172830 A1 | 7/2013 | Hunter et al. | |
| 2013/0206857 A1* | 8/2013 | Ivri | F04B 43/046 |
| | | | 239/4 |
| 2013/0299607 A1 | 11/2013 | Wilkerson et al. | |
| 2013/0053042 A1 | 12/2013 | Ferreri et al. | |
| 2014/0113946 A1 | 4/2014 | Abad | |
| 2014/0171490 A1 | 6/2014 | Gross et al. | |
| 2014/0187969 A1 | 7/2014 | Hunter et al. | |
| 2014/0214024 A1 | 7/2014 | Eichler | |
| 2014/0224267 A1 | 8/2014 | Levitz et al. | |
| 2014/0242022 A1 | 8/2014 | Vehige et al. | |
| 2014/0249491 A1 | 9/2014 | Ballou, Jr. et al. | |
| 2014/0257172 A1 | 9/2014 | Yalamanchili | |
| 2014/0274910 A1 | 9/2014 | Cumberlidge et al. | |
| 2014/0276054 A1 | 9/2014 | Hossack et al. | |
| 2014/0285121 A1 | 9/2014 | Balogh et al. | |
| 2014/0336618 A1* | 11/2014 | Wilkerson | A61F 9/0008 |
| | | | 604/521 |
| 2015/0018781 A1 | 1/2015 | Rinderknect et al. | |
| 2015/0097050 A1 | 4/2015 | Ciervo | |
| 2015/0139973 A1 | 5/2015 | Steinfeld et al. | |
| 2015/0276994 A1 | 10/2015 | Shen et al. | |
| 2015/0328151 A1 | 11/2015 | Ballou, Jr. et al. | |
| 2016/0120833 A1 | 5/2016 | Wan et al. | |
| 2016/0199225 A1 | 7/2016 | Ivri | |
| 2016/0296367 A1 | 10/2016 | Ivri | |
| 2016/0354559 A1 | 12/2016 | Gavini et al. | |
| 2017/0028626 A1 | 2/2017 | Delrot et al. | |
| 2017/0136484 A1 | 5/2017 | Wilkerson et al. | |
| 2017/0151088 A1 | 6/2017 | Ballou, Jr. et al. | |
| 2017/0156927 A1 | 6/2017 | Richter et al. | |
| 2017/0182510 A1 | 6/2017 | Wilkerson et al. | |
| 2017/0187969 A1 | 6/2017 | Kitamori et al. | |
| 2017/0274159 A1 | 9/2017 | Gavini et al. | |
| 2017/0344714 A1 | 11/2017 | Ballou, Jr. et al. | |
| 2018/0085251 A1 | 3/2018 | Hunter et al. | |
| 2018/0116871 A1 | 5/2018 | Hunter et al. | |
| 2018/0207030 A1 | 7/2018 | Ivri et al. | |
| 2019/0053945 A1 | 2/2019 | Hunter et al. | |
| 2019/0074086 A1 | 3/2019 | Ballou, Jr. et al. | |
| 2019/0099071 A1 | 4/2019 | Ehrmann | |

FOREIGN PATENT DOCUMENTS

| | | |
|---|---|---|
| JP | 3055480 U | 1/1999 |
| WO | WO 2001/046134 | 6/2001 |
| WO | WO 2013/090459 | 6/2013 |

(56) References Cited

FOREIGN PATENT DOCUMENTS

| WO | WO 2013/090468 | 6/2013 |
|---|---|---|
| WO | WO 2013/155201 | 10/2013 |
| WO | WO 2013/158967 | 10/2013 |
| WO | WO 2016/115050 | 7/2016 |
| WO | WO 2016/164830 | 10/2016 |
| WO | WO2019113483 A1 | 6/2019 |

OTHER PUBLICATIONS

Murube, J. et al., "Classification of artificial tears: II. Additives and commercial formulas," Adv Exp Med Biol., 438:705-715, 1998.

Jow, U. et al., "Design and Optimization of Printed Spiral Coils for Efficient Transcutaneous Inductive Power Transmission" *IEEE Transactions On Biomedical Circuits And Systems*, vol. 1, No. 3, pp. 193-202, Sep. 2007.

Oxford online dictionary entry for "stream", https://en.oxforddictionaries.com/definition/us/stream, Accessed Thu Dec. 13, 2018.

Macmillan online dictionary entry for "stream", https://macmillandictionary.com/dictionary/american/stream_1#stream_9, Accessed Thu Dec. 13, 2018.

Vocabulary.com online dictionary entry for "stream", https://www.dictionary.com/stream, Accessed Thu Dec. 13, 2018.

Choi et al., Generation of controllable monodispersed sprays using impulse jet and charging techniques, Review of Scientific Instruments 61, 1689 (1990).

Lindblad et al., Production of uniform-sized liquid droplets, Journal of Scientific Instruments, vol. 42, No. 8, 1965.

Lux et al., A Comparative Bioavailability Study of Three Conventional Eye Drops Versus a Single Lyophilisate, British Journal of Ophthalmology, Apr. 2003, vol. 87, No. 4, p. 436-440.

Abidie et al., Lifitegrast: A Novel Drug for Treatment of Dry Eye Disease, Journal of Pharmacology and Pharmacotherapy, Oct.-Dec. 2016, vol. 7, No. 4, p. 194-198.

Ali et al., Glaucoma and Dry Eye, Ophthalmology, Jun. 2009, vol. 116, No. 6, p. 1232.

Kent, Getting Meds onto the Eye, 21st Century Style, Review of Ophthalmology, Mar. 15, 2013, https://www.reviewofophthalmology.com/article/getting-meds-onto-the-eye-21st-century-style, p. 1-6, accessed Aug. 27, 2019.

Lallemand et al., Cyclosporine A Delivery to the Eye: A Comprehensive Review of Academic and Industrial Efforts, European Journal of Pharmaceutics and Biopharmaceutics, Aug. 2017, vol. 117, p. 14-28.

* cited by examiner

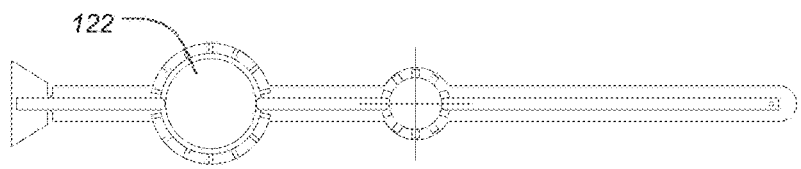
FIG-5B
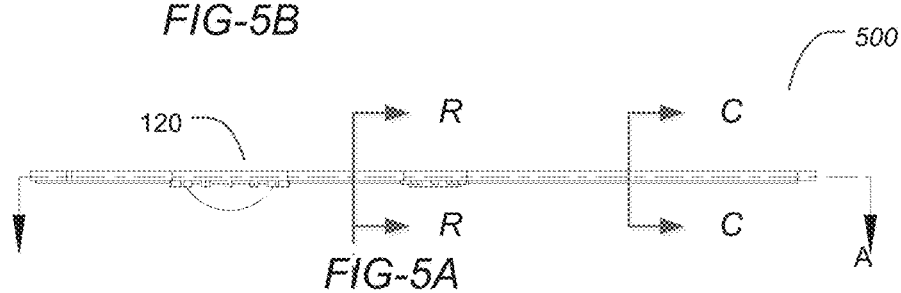
FIG-5A
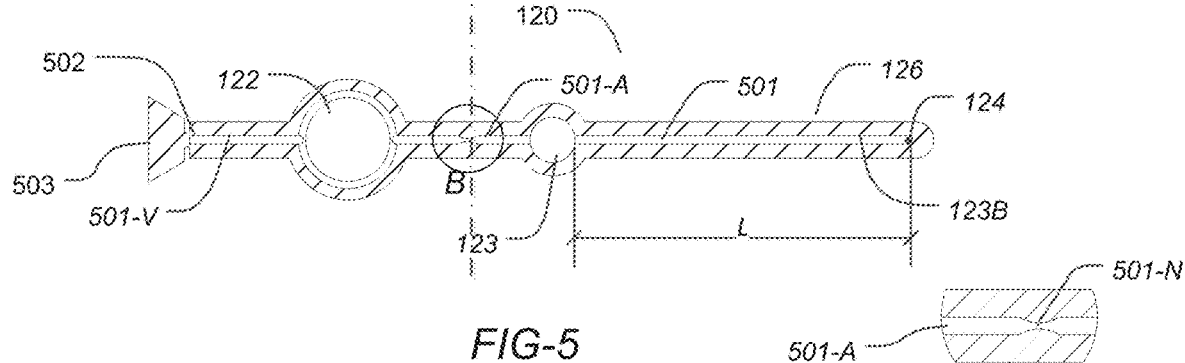
FIG-5
FIG-5C

PIEZOELECTRIC DISPENSER WITH REPLACEABLE AMPOULE

CROSS-REFERENCE TO RELATED APPLICATIONS

This application claims the benefit of priority to U.S. Prov. App. 62/178,464 filed Apr. 10, 2015, which is incorporated herein by reference in its entirety.

FIELD OF THE INVENTION

The present invention relates to devices for ejecting fluid stream specifically but not exclusively for topical administration of ophthalmic therapeutics.

BACKGROUND OF THE INVENTION

A typical medical eye dropper dispenses single drops which have large volumes, typically about 50 µL. However, since the human eye can typically retain only 7 µL of fluid on the corneal surface at a time, larger volume results in overflow and loss of part of the medication from the eye surface. In addition, a large volume of a single drop, such as 30 or 50 µL, causes a blinking reflex which removes majority of the fluid from the cornea, and inconvenience which leads to poor compliance. U.S. Pat. Pub. 2012/0070467 A1 (incorporated herein by reference in its entirety) describes a droplet generating device for drug delivery to the eye which comprises a piezoelectric actuated droplets generator for delivering small droplets to the eye. This device operates on the principle of nebulizers which use a vibrating plate with multiple apertures to generate aerosol. Such ejector mechanisms are integrally coupled to a fluid reservoir which is periodically refilled by the user. Refilling, however, carries the risk of bacterial contamination and the risk of ocular infection. Generally, drug filling, particularly for ophthalmic use, must be processed in tightly controlled aseptic environment which is not available to the user. Another problem associated with the aerosol delivery as described in the prior art is the user ability to direct the aerosol stream to the surface of the eye. Any misalignment of the dispensing device with the eye will result is inaccurate dosing.

The present invention provides a devices for ejecting therapeutic fluid to surface of the eye or to the conjunctival tissue. The device advantageously utilizes a disposable sterile drug ampoule which can be attached to and detached from a piezoelectric actuator, thereby eliminating the need of refilling and mitigating the possibility of bacterial contamination and providing a cost effective approach reusing the piezoelectric actuator for further operation. The invention further provides a delivery of a single stream and a mechanism to align the stream to the eye prior to actuation to assure convenient and precise dosing. Surprisingly, it has been found that delivery of a single stream imparts lesser impact on the eye and is therefore is more convenient to use when compared to delivery of a mist or a distribution of small droplets which has the same accumulated volume. Unlike a mist or spray, a single stream can be precisely oriented to target a specific location on the surface of the eye or the conjunctival tissue. This characteristic is largely attributed to the aerodynamic behavior of the stream. Specifically, delivery of a mist generally produces a turbulence which causes divergence of the droplet from the target while a stream pierces through the air and reach the target area more precisely.

SUMMARY OF THE INVENTION

The invention provides a miniature fluid ejection device for treatment of ophthalmic diseases by topical administration. The device comprises a piezoelectric actuator and separable disposable drug or fluid package. The piezoelectric actuator is configured to transmit energy to the drug or fluid package such as acoustic energy or oscillation. The device is characterized in its drug packaging which can be easily attached to or detached from the piezoelectric actuator. Empty drug or fluid packages are disposed, thereby eliminating the need for filling the drug by the user and the risk of bacterial contamination.

The drug or fluid package is configured to dispense micro-droplets by one or more acoustic pulses exerted by the piezoelectric actuator onto the external surface of the disposable drug package. The drug package can be decoupled from the piezoelectric actuator allowing disposal of used packages while the piezoelectric actuator is subsequently reused with another drug or fluid package. The invention provides a cost effective approach for topical drug delivery to the eye.

The piezoelectric actuator is a small module which can be used as a handheld device or as an attachment to an eyewear article such as optical or sunglasses. In one embodiment the drug or fluid package is comprised of a blow-fill-seal package or an ampoule containing an ophthalmic formulation.

U.S. Pat. Pub. 2012/0070467 (the entirety of which is hereby incorporated by reference herein and for any purpose) describes examples of various ophthalmic compositions and therapeutics which may be used with the devices and methods described herein.

The drug or fluid package is made of a thermoplastic polymer such as polyethylene, terephthalate, polyethylene or polypropylene. The drug or fluid package includes a drug reservoir and an aperture plate containing one or more apertures. The drug or fluid package further includes fluid channel which connects between the drug reservoir and the aperture plate. Drug or fluid package contains ophthalmic formulations which fills the volume of the drug reservoir and the channel. Drug or fluid package optionally includes a valve that is configured to seal the opening of the aperture plate to prevent or minimized bacterial contamination. The valve may be open by mechanical mechanisms simultaneously when the device is electrically actuated.

Droplet volumes are generally between, e.g., 100 to 1000 pL, and the size of the aperture is typically between, e.g., 10 to 100 micron In some embodiments the dispensing device includes an optical mechanism to align or target the dispensing aperture to the ocular surface or to the area of the lower conjunctiva prior to actuation. Such alignment assures that the entire dose reaches the surface of the eye. The alignment mechanism may include a collimated beam of light with visible wavelength generated by, e.g., LED, laser or a lamp. For example, it may include a tubular member with proximal and distal openings; the distal opening may be positioned near a light source while the proximal opening of the tube is brought into proximity near the eye of the user. Prior to actuation of the dispensing device, the user may align the eye to be treated with the proximal opening of the tube and then manipulate the orientation of the device until the light at the distal end of the tube becomes visible. In this way the device is brought to an alignment with the optical axis of the eye to be treated or the center of the pupil. The dispensing nozzle is positioned at a predetermined small offset relative to the optical axis of the tube. When the device is actuated, a stream of fluid will reach the targeted surface of the eye or the conjunctival tissue and will deposit fluid at the above mentioned offset from the pupil.

The optical tube may have a length of, e.g., 20, 30, or 40 mm while its internal diameter ranges between, e.g., 1 to 5 mm. Preferably, the internal surfaces of the tube are coated with optically-black non-reflective coating.

A typical volume of, e.g., 4 to 10 µL, may be delivered during the eye fixation time, typically under 1 second, and preferably within 250 ms. In one embodiment the dispensing device includes one or more apertures but typically less than, e.g., 20 apertures, and preferably less than, e.g., 10 apertures and most preferably a single aperture. The apertures are positioned in a predetermined offset relative to the optical axis of the alignment tube. This offset determines where the fluid stream is deposited relative to optical axis of the eye or relative to the center of the pupil or the center of the iris. Typically, the offset may be, e.g., 2-20 mm, from the center of the pupil in the vertical or horizontal directions, or in both vertical and horizontal directions.

The drug or fluid package can be removed and replaced, while the piezoelectric actuator can be reused with another drug package. In one embodiment the drug or fluid package is manufactured by an aseptic blow-fill-seal process commonly used in packaging of pharmaceutical liquids. Such processes are described for example in U.S. Pat. Pub. 2013/0345672 A1; 2012/0017898; and U.S. Pat. No. 5,624,057, each of which is incorporated herein by reference in its entirety and for any purpose.

The device further includes an electronic circuit that is configured to generate and transmit an electric pulse or wave form to the piezoelectric actuator. The circuit may be comprised of a half-bridge driver which generally includes a half-bridge driver chip and two MOSFET transistors. The half-bridge driver receives an input signal and transmits a switching output which drives a pair of MOSFET transistors sequentially "on" and "off". In this way it translates the low voltage input signal to a high power electrical pulse that is capable of driving the piezoelectric actuator. The circuit may further include an inductor that increases the output to higher voltage level. Preferably the inductance of the inductor and the capacitance of the piezoelectric actuator may be tuned to operate in resonance at the selected output frequency. The input signal which transmitted to the half bridge driver chip may be generated by a microprocessor or by a signal generator IC (integrated circuit). In one embodiment the driver, the transistors and the microprocessor are fabricated on a single integrated circuit. Preferably such IC is attached and encapsulated directly to a printed circuit board (PCB) utilizing a chip-on-board (COB) packaging process. In the field of microelectronics COB is used to reduce the size of the circuit. The input voltage of the circuit is preferably below, e.g., 5 volts, and more preferably below, e.g., 3 volts, and even more preferably below, e.g., 1.5 volts. The source of energy may be provided by a power supply such as capacitors, batteries, etc. which may be optionally rechargeable. When the circuit is driven sequentially "on" and "off" as described earlier the fluid stream emits from the aperture as individual droplets. However, when an inductor is added and is tuned to operate at the electrical resonance of the circuit then the electrical output becomes sinusoidal and the fluid emits as a collimated and continuous stream without individual droplets.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 5 illustrate a section view marked as Detail-A through the acoustic cavity of the drug package showing a cross sectional shape of the acoustic cavity clamped by the piezo chip in accordance with certain embodiments of the invention.

FIGS. 5A to 5C illustrate side, top and detail cross-sectional views of the drug package and acoustic cavity.

DETAILED DESCRIPTION OF THE INVENTION

The preferred embodiments of the invention described herein relates to a device for drug delivery to the ocular surface for treatment of ophthalmic diseases. In the systems and methods described herein droplets are dispensed in high frequency but in a single drop format or in a continuous stream depending on the electric signal input as described earlier. When droplets are produced they generally have ultra small volumes ranging from about a few hundred pico-liters to about one nano-liters. Generally, droplets of such volume or continuous collimated single stream do not cause blinking reflex.

In the first aspect embodiments the dispensing devices advantageously utilize a disposable, removable or separable drug or fluid package while desirably retaining the piezoelectric actuator or transducer for subsequent further uses, thereby providing an economical and cost effective approach with reuse of the piezoelectric actuator or transducer for further operation.

Figure 1:
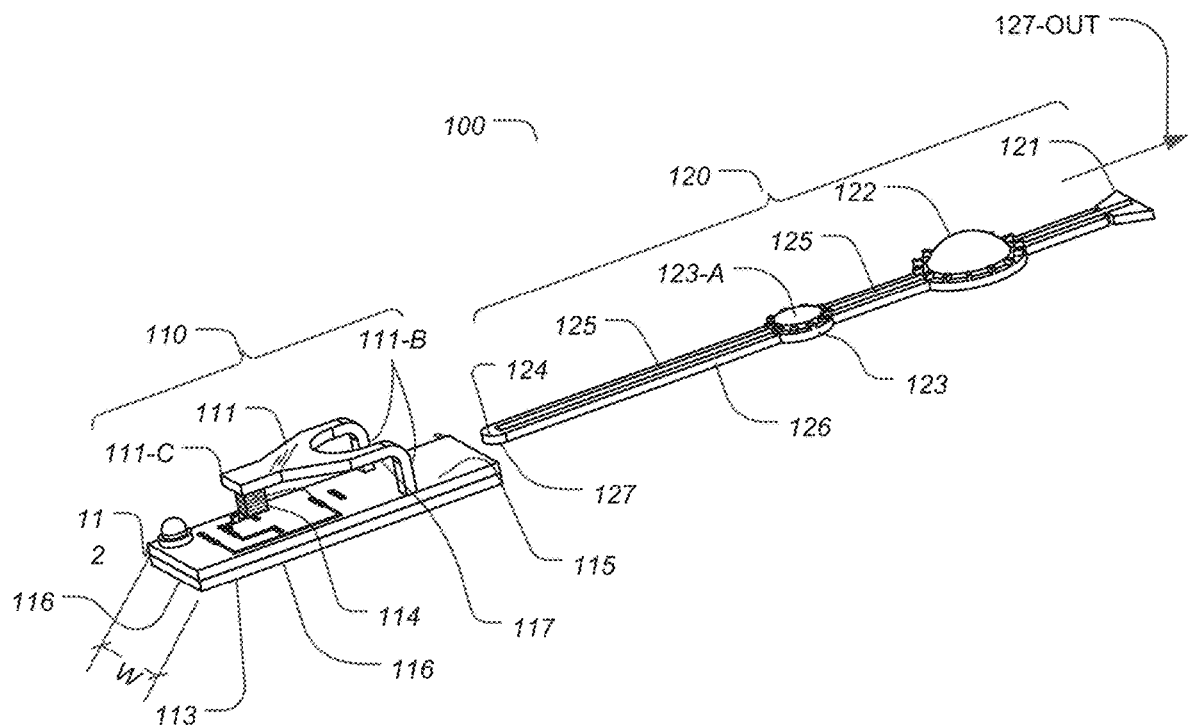
FIG. 1 is a simplified exploded view of piezoelectric actuator and the drug package being operable to dispense droplets by an acoustic pulse.
Figure 2:
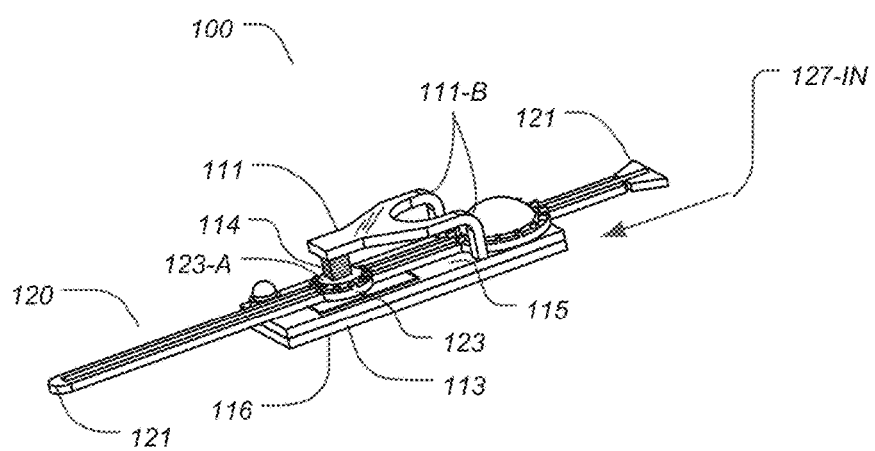
FIG. 2 is a simplified view of the piezoelectric actuator and the drug package operatively coupled in accordance with certain embodiments of the invention.

FIG. 1 and FIG. 2 illustrate a piezoelectric actuator (110) in accordance with some embodiments. The piezoelectric actuator is comprised of a piezoelectric chip (114) that is operatively coupled to a drug or fluid package (120) under preloading force. Actuator (110) is configured to generate an acoustic pressure within the drug or fluid package to dispense droplets of ophthalmic composition from aperture (124) to the corneal surface of the eye. Piezoelectric actuator (110) can be coupled or decoupled from the drug package as shown in FIG. 1 and FIG. 2 and as discussed further below and herein.

As illustrated in FIG. 1, the device (100) includes a drug or fluid package (120) and piezoelectric actuator (110). Drug or fluid package (120) is comprised of thermoplastic body which includes a blister (122) containing ophthalmic composition to be dispensed. Drug or fluid package (110) further includes an elongated nozzle or conduit (126) which extends from the blister and terminates at the tip section (127). Conduit (126) includes an internal fluid channel (not shown) which is in fluid communication with the blister (122). Conduit (126) further includes a dispensing aperture (124) proximal to tip (127) and an acoustic cavity (123) distal to the tip and proximal to the blister (122). In some embodiment the distance between blister (122) and acoustic cavity is about 5-15 mm and the distance between acoustic cavity (123) and aperture is between 30-60 mm. In this way, the piezoelectric actuator (110) is conveniently distal to the dispensing aperture (124) or the eye.

Acoustic cavity (123) comprising a cylindrical chamber sealed by a thin-wall membrane (123-A). Drug or fluid package (120) is configured to dispense a micro-droplet each time a pulse displacement is exerted by the actuator (110) onto the surface of the thin-wall membrane (123-A). Such pulse displacement generates an acoustic pressure within the acoustic cavity (123) which then propagates through the fluid in conduit (126) toward the aperture (124) whereas droplets are dispensed in a single drop format to the surface of the eye.

Piezoelectric actuator (110) comprising a piezoelectric clamp and an electronic circuit. The piezoelectric clamp is configured to apply pulse displacements to the acoustic cavity while it is being clamped under spring pressure.

Piezoelectric actuator (110) includes a printed circuit board (PCB) (115) capable of generating electrical pulses at a selected frequency. Referring to FIG. 2 it can be seen that PCB (115) also functions as rigid substrate for supporting the drug or fluid package (120) while being preloaded by the piezoelectric chip (114). It can be seen the piezoelectric chip (114) is attached to the free end of an "L" shape spring member (111) while the opposite end of the spring is split to two legs (111-B) each is attached to the PCB by a solder joints. The piezoelectric chip (114) is attached to the free end (111-C) by a structural epoxy adhesive such as, but not limited to, LOCTITE® Hysol® type E-30CL. Spring member (111) is dimensioned to preload the piezo chip (114) against surface (123-A) by applying about of 5-10 Newton. In some embodiments the spring member (111) is made of beryllium cupper. In some embodiments spring member (111) is made of spring steel with nickel plating. The thickness of spring is in the range of 0.3-0.7 mm.

Drug or fluid package (120) may be inserted into, or removed from actuator (110) in the directions indicated by arrows (127-IN) and (127-OUT). FIG. 1 illustrates an exploded view of device (100) showing the drug package (120) decoupled from the piezoelectric actuator (110) and FIG. 2 illustrates the drug or fluid package (120) operatively coupled to actuator (110).

Piezoelectric chip (114) comprises of a monolithic co-fired piezoceramic stack model PA3CE sold by Thorlabs Inc., Newton, N.J., USA. The chip expands and contracts under the input of an alternating voltage. Co-fired piezoceramic stack produces large displacement, generally in the range of 1-5 micron. In comparison a single crystal piezoceramic element, produces a displacement in the range of a 0.1-0.5 micron, therefore normally requires structural attachment to the oscillating structure. Thus, the co-fired piezo-ceramic stack enables the separation of the drug or fluid package and an economical, cost effective and practical solution.

In one embodiment the device may have one or more apertures. Typically the diameter of each aperture is in the range of 10-120 micron.

Figure 3:
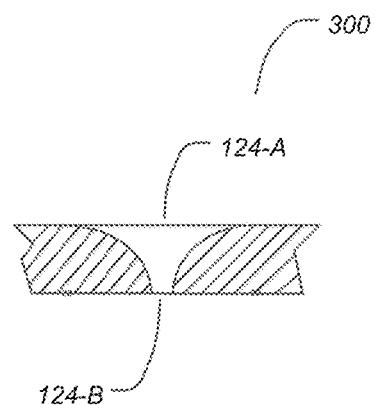
FIG. 3 is a cross sectional view of the dispensing aperture in accordance with certain embodiments of the invention.
Figure 4:
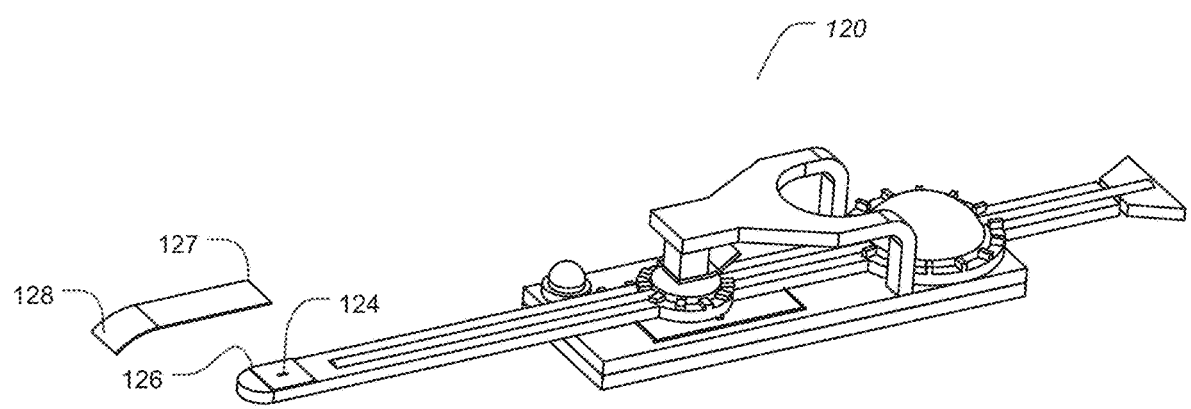
FIG. 4 is an exploded view of the piezoelectric actuator showing the aperture sealing method.

FIG. 3 illustrates the cross sectional shape of each aperture. It can be seen that the aperture has a generally tapered or flared mouth shape whereas the large opening (124-A) is the fluid inlet and the small opening (124-B) is the droplet outlet. In some embodiments the apertures are formed separately on a polyamide film such as Mylar™ or Kevlar™ (DuPont, Wilmington, Del. USA). The apertures are etched using a laser ablation process commonly used in fabrication of inkjet nozzle plate. FIG. 4 illustrates the polyamide film (126) with the apertures (124). The film is attached by to the drug or fluid package by pressure-sensitive adhesive. Drug or fluid package (120) further includes a sealing tape (127) that is adhesively attached to a polyamide film (126) over the aperture (124) to hermetically seal the drug or fluid package (120) and to prevent bacterial contamination during storage. Sealing tape (127) may be peeled off shortly before drug cartridge is used. Conveniently, the edge (128) of the sealing tape (127) is extended from the edge of drug package, in this way the sealing tape may be easily peeled off by pulling on the extended edge (128) shortly before use. Sealing tape (127) may be labeled to indicate that it should be removed before the drug package is used.

FIG. 5 and FIG. 5A illustrates a cross sectional view through the thickness of drug or fluid package (120) in the direction indicated in by arrows A-A. FIG. 5 illustrates a cross sectional view showing the fluid channel (501) that extends along drug or fluid package (122) from drug reservoir (122) through acoustic cavity (123) and to aperture (124) The section of channel (501) that extends between the drug reservoir (122) and the acoustic cavity (123) is shown in an enlarged detailed view in FIG. 5C marked Detail-B.

Referring to FIG. 5C it can be seen that the section of the channel that connects between the drug reservoir (122) and the acoustic cavity (123) has a restriction (501-N). Restriction (501-N) restricts the propagation of acoustic pressure wave from acoustic cavity (123) to reservoir (122). This limits the acoustic pressure dissipation into the drug reservoir and the pressure wave that reaches the aperture (124) is desirably more intense In some embodiment the cross section area of channel (501) is between 0.25-1 mm while cross section of the restricted section (501-N) is about 50-90% smaller. The cross sectional area of the restriction (501-N) is the effective area through which the acoustic wave propagates as indicated by the arrow symbol R-R and C-C. The cross sectional shape may be but is not limited to circulator or rectangular shape.

The end section of channel (501) is used as a venting port to the drug reservoir (122). The end section of the channel (501-V) extends from the drug reservoir to tab section (503). Before use the tab is broken and the opening of channel (501-V) is exposed to the atmosphere. Venting is necessary to prevent vacuum build up in the drug reservoir during use. The vent is made from porous polyethylene plug which filters out particles larger than, e.g., 0.2 micron such as airborne microorganisms and the like.

In some embodiment the diameter of the drug reservoir (122) is between, e.g., 8 mm to 14 mm, and its volume is in the range between, e.g., 0.5 mL to 3.0 mL (3000 µL). In some embodiment the diameter the acoustic cavity is between 5-8 mm and its volume is 30-100 µL The length of the channel (501) between the acoustic cavity (123) and the aperture (114) is designated by the letter L in FIG. 5. In some embodiments the operating frequency is the natural frequency of the fluid in the channel (501). The natural frequency is govern by the following equation:

$$f := \frac{i \cdot C}{2 \cdot L} \quad (1)$$

C=1500 m/sec (speed of sound in aqueous composition)
L=40 mm (length L of the channel (501))
i=1, 2, 3, . . . , n When substituting C, L and i=1 it can be found that the natural frequency of the fluid in the channel (501) is 19,500 Hz, therefore the operating frequency of the electronic circuit should also be 19,500 Hz. The volume of liquid dispense is determined by the number of cycles that the piezoelectric actuator operates in this frequency.

All the internal fluid passage shown in cross sectional view of FIG. 5 including fluid channels (501), drug reservoir (122) and acoustic cavity (123) are treated with hydrophilic coating which increase the surface tension produces a strong capillary force through all the internal fluid passages of the drug or fluid package (120) as well as strong fluid-solid coupling in the acoustic cavity. Particularly effective coating is Hydrophil™ made by Lotus Leaf Coating Inc. New Mexico, USA.

$$L := \frac{\left(\frac{1}{2 \cdot \pi \cdot f}\right)}{C} \quad (2)$$

where, L=2.22 mH

An inductor that has a value of 2.22 mH connected in series to the piezo chip will cause the circuit to resonate and as a result the voltage level of the battery will increase typically by, e.g., 5, 10, 20 times. In the present invention the size of the droplets is in the range of 500 pL (pico-Liter). In comparison, the lachrymal tear flow is about 1 µL/min, thus such volume can be created by generating, e.g., 2000 pulses at a frequency of 19,500 Hz during a period of about 0.1 sec.

Figure 6:
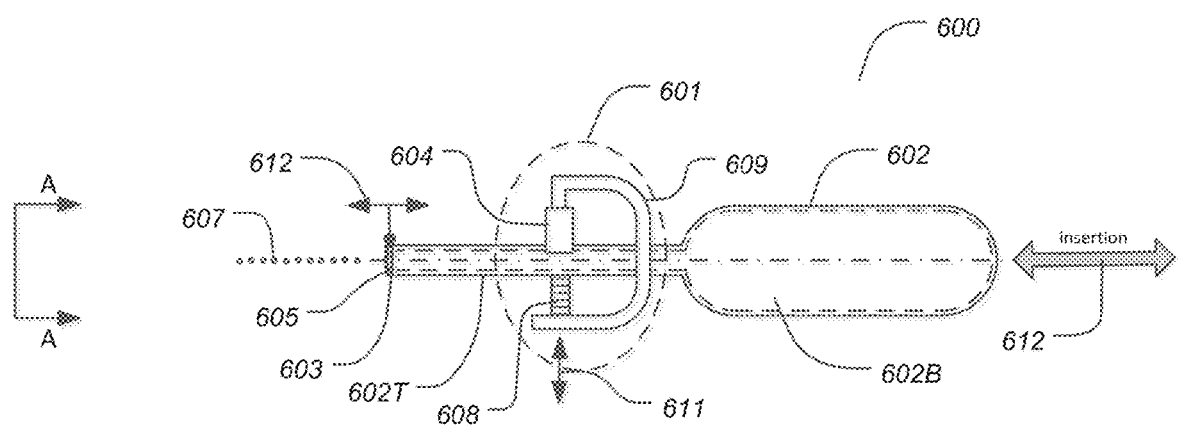
FIG. 6 illustrates a dispensing ampoule which utilizes a longitudinal pulse and aperture plate.

FIG. 6 illustrates an alternative dispensing device which is based in part on the dispensing principle described in U.S. Pat. Pub. 2012/0304929 A1, the entirety of which is hereby incorporated by reference herein and for any purpose.

Embodiments of the dispensing devices advantageously utilize a disposable, removable or separable ampoule or vial while desirably retaining the piezoelectric actuator or transducer for subsequent further uses, thereby eliminates the need for the user to refill drug, mitigating the possibility of bacterial contamination and providing an economical and cost effective approach with reuse of the piezoelectric actuator or transducer for further operation such as with a variety of ophthalmic therapeutics.

FIG. 6 illustrates a drug ampoule (602) and a piezoelectric transducer (601). The ampoule comprises of a drug blister (602B) and a tube (602T) which includes an aperture plate (605) attached to the end of the tube. The transducer (601) generally comprising an attachment mechanism in the form of a C-clamp (609) having a piezoelectric chip (608) on one side of the clamp and an anvil (604) on the opposite side of the clamp. The clamp is coupled to tube (602T) of the ampoule (602) as discussed further below and herein.

The preloading C-clamp (601) and the ampoule (602) are engaged in slight pressure interference fit which allows them to be engage or disengaged by applying an axial pulling or pushing force illustrated by the arrow (612). Conveniently the pulling or pushing force is smaller than, e.g., 10 Newton.

In operation, a burst of voltage pulses actuates the piezoelectric chip (608) so that it expands and contracts toward the anvil (604) while radial force (611) is exerted or applied on the wall of the tube (602T). This radial force (611) causes a small deformation and radial displacement of the wall of the tube. Further, acoustic stress wave propagates or is transmitted axially or longitudinally from the clamp region of the tube, through the wall of the tube (602T) and toward the tube tip (603) which undergoes axial or longitudinal motion, displacement or movement in the axial direction (612). Thus, a stress or pressure wave passes longitudinally or axially through the tube wall and provides for transmission or conversion of tube radial motion (611) to axial or longitudinal motion (612) at the tip of the tube (603).

On completion of one cycle, the tube (602T) reverts back to its deactivated state with radially outward tube motion (611) and retracting tube tip axial motion (612). When multiple pulses of an alternating voltage cause expansion and contraction of the piezoelectric chip (608) the tube tip (603) undergoes multiple axial or longitudinal oscillations. The axial oscillation oscillates the aperture plate (605) which causes fluid droplets (607) to be ejected from the aperture plate (605).

While the fluid which is ejected from the aperture plate in this and other embodiments may be described as droplets, the ejected fluid may be emitted as individual droplets separated from one another or the ejected fluid may be emitted as a continuous stream of fluid with no separation until the transducer is no longer actuated (or until the fluid runs out). The emission of the continuous stream of fluid may be implemented in this embodiment or any of the other embodiments described herein.

Figure 6A:
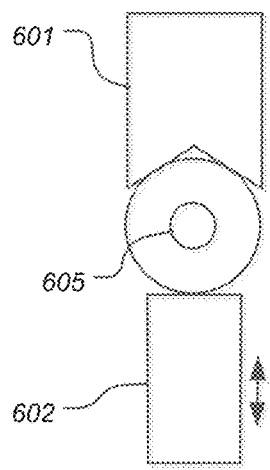
FIG. 6A illustrates a frontal view of the piezoelectric actuator described in relation to FIG. 6.

FIG. 6A illustrates a frontal view of embodiment (600) showing the anvil (601) and the piezoelectric chip (602). It can be seen that the anvil engages with the tube by a V shape groove which assists in properly constrain the tube to the anvil.

Typically the external diameter of the tube is about, e.g., 1-4 mm, and the inside diameter is between, e.g., 0.5 to 2.5 mm.

Figure 7:
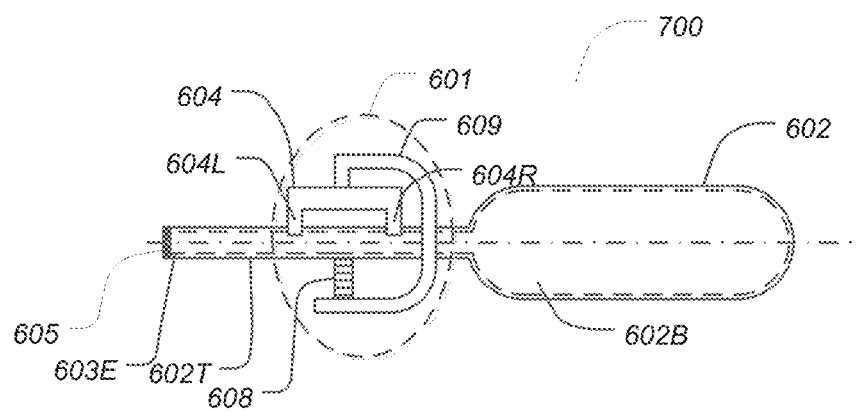
FIG. 7 illustrates a dispensing ampoule which is configured to utilize a combination of longitudinal and axial pulses.
Figure 7A:
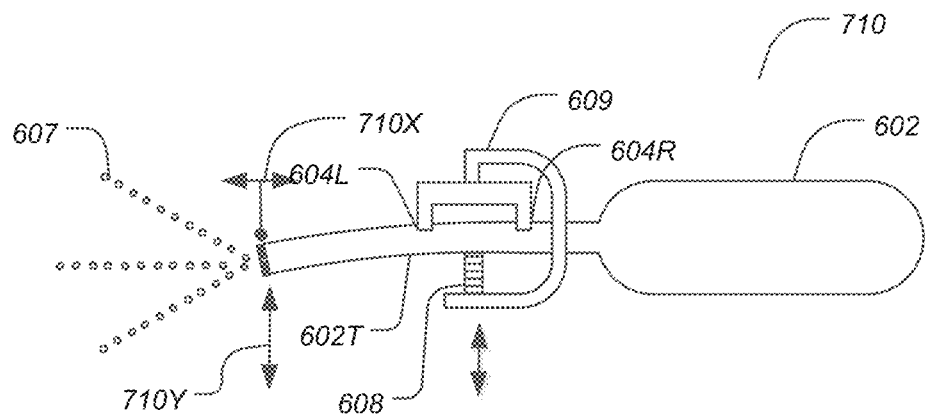
FIGS. 7A and 7B illustrate a dispensing ampoule dispensing a drug via the combination of longitudinal and axial pulses.
Figure 7B:
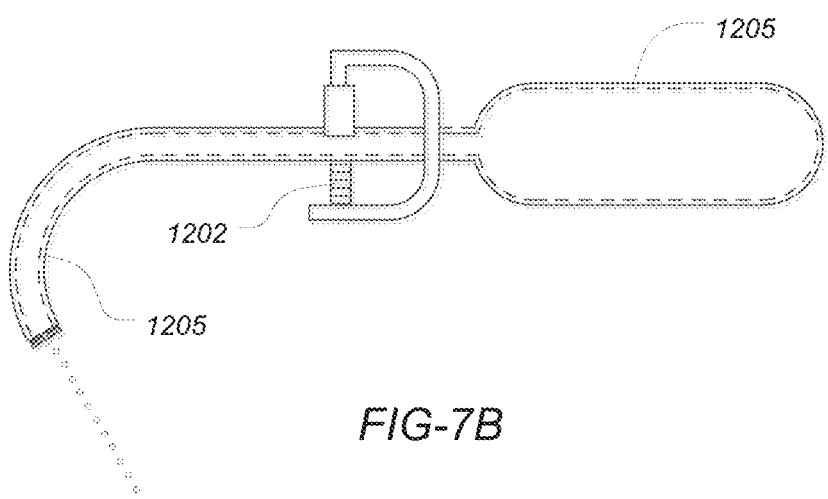

FIG. 7 and FIG. 7A illustrate an alternative preferred embodiment comprising a transducer which is configured to disperse the steam of droplets in a fan-shaped spray pattern. Such dispersion reduces the impact force of the fluid on the corneal surface reducing blinking reflex and providing more convenient treatment. It can be seen that anvil (604) has a U-shape with two engagement arms (604A) and (604B) while the piezoelectric chip (608) is positioned at the opposite side of the clamp between the two engagement arms of the anvil (604). In this way the displacement of the piezoelectric chip tend to cause a bending motion of the tube (602T) in addition to the axial displacement as described earlier. As a result, droplets (607) are accelerated both in axial and radial directions which therefore produces a conical or a fan-shaped pattern. Such distribution reduces the impact force of the droplet on the corneal surface.

Figure 8:
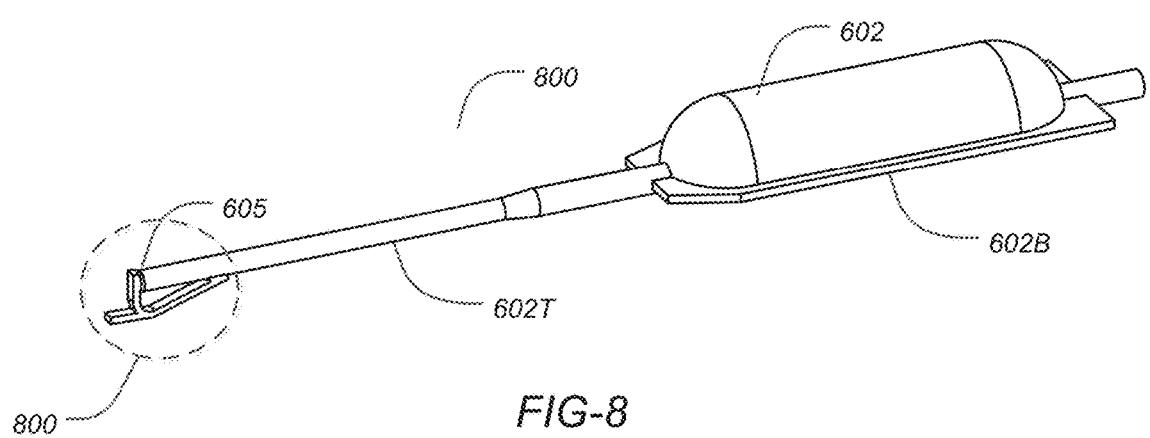
FIG. 8 illustrates a dispensing ampoule with a valve shown in a closed position.
Figure 8A:
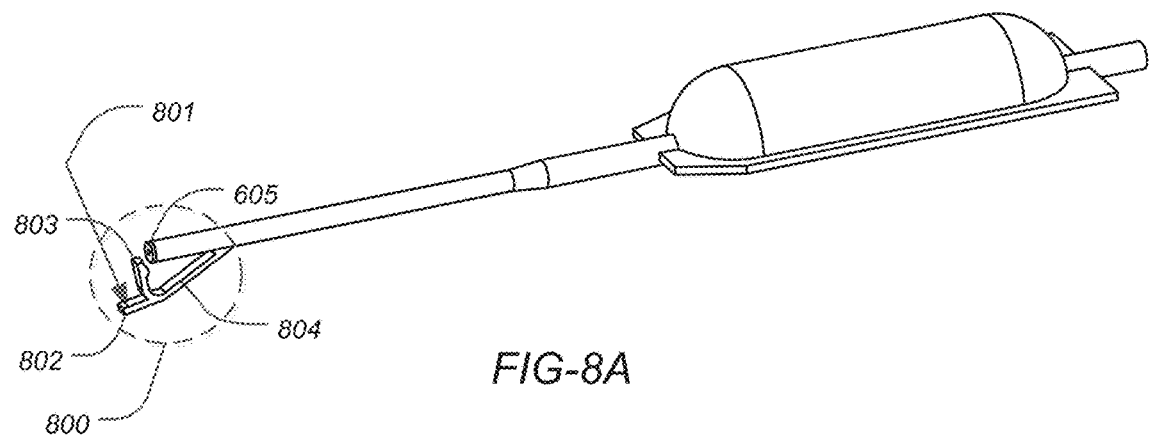
FIG. 8A illustrates the dispensing ampoule with a valve shown in an opened position.

FIG. 8 and FIG. 8A illustrate a disposable ampoule (800) that may be used in any of the dispensing embodiments. Ampoule (602) includes a shut-off valve (800) which seals the opening of the aperture plate (605) to prevent or reduce bacterial contamination through the opening of the aperture. The mechanical valve opens upon activation of the piezoelectric actuator. As will explain further below, a mechanical linkage is provided to operate an electronic switch simultaneously with the valve (800). Valve (800) included sealing member (803), a flexible linkage (804) and a push-on pedestal (804). As illustrated, actuation force (801) which is applied on the pedestal (802) bends the flexible linkage (804) thereby moves the sealing member (803) away from the aperture. Vector (801) illustrates the force and direction to open valve (800). Ampoule (602) may contain, e.g., 0.5, 1, 2, 3, or 4 mL, of fluid but typically less than, e.g., 5 mL. Aperture plate may include one or more apertures, typically in the range of, e.g., 10-80 micron. The size of the apertures is generally depending on the viscosity and the rheology of the fluid in use. The diameter of the aperture plate (605) is typically, e.g., 1.5, 2, 3, 4 mm, but generally less than, e.g., 5 mm. The number of apertures and their diameter is dependent of the rheology of the liquid and is generally configured to deliver a dose of, e.g., 7-10 microliter, to the ocular surface within, e.g., 50 to 1000 ms.

Figure 9:
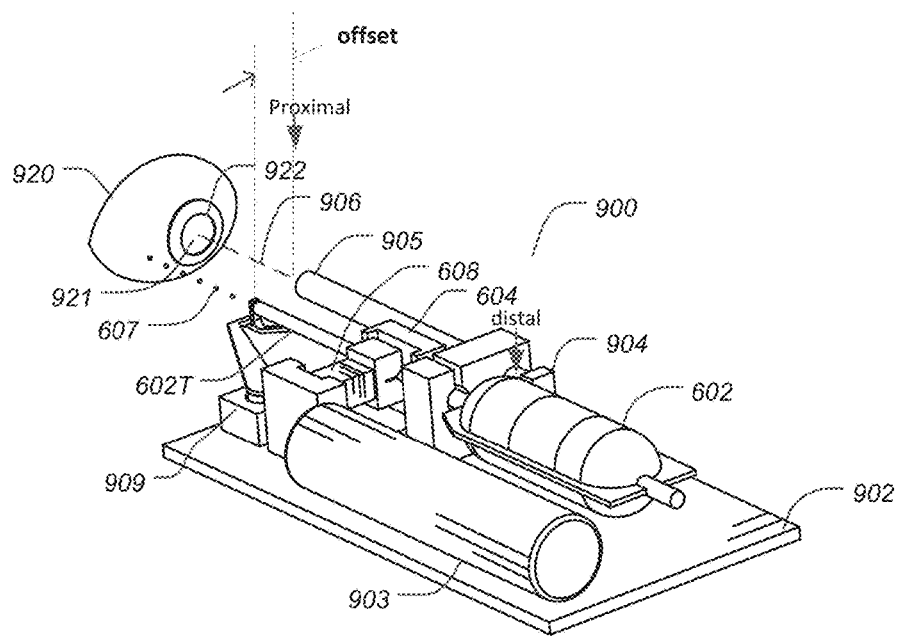
FIGS. 9 and 9A illustrate isometric views of the assembly of the piezoelectric actuator described in certain embodiments of the present invention.
Figure 9A:
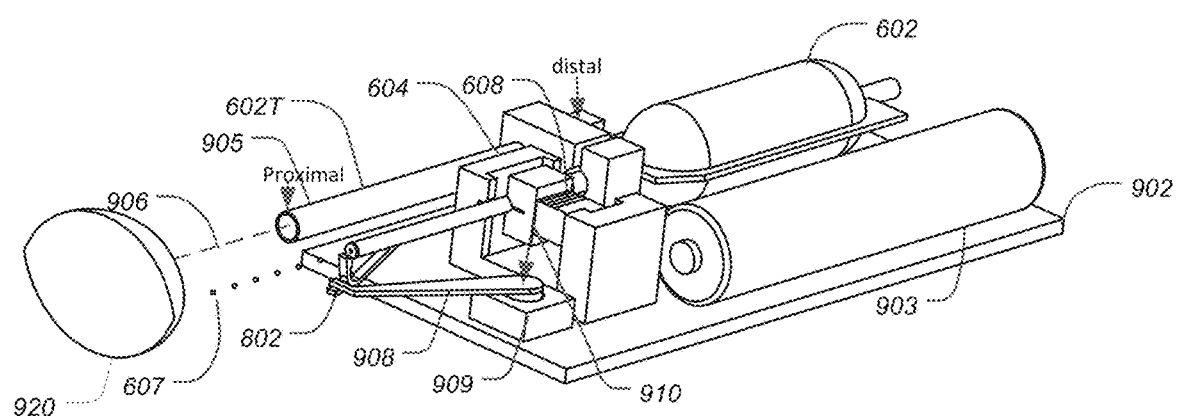

FIG. 9 and FIG. 9A illustrate two perspective views of an assembly of the dispensing device as explained earlier in relation FIG. 7 (with corresponding numbers to FIG. 7). Assembly (900) illustrates the piezoelectric actuator (608) and drug ampoule (602) which includes a valve as discussed in relation to FIG. 8. Dispensing device (900) further includes an optical means to align or target the dispensing aperture to the ocular surface of the eye (920) prior to actuation. Such alignment assures that the stream of droplets or a continuous stream of fluid (607) emitting from the aperture will reach the surface of the eye. The alignment mechanism may comprise a tube member (905) having one opening proximal to the eye and a second openings distal to the eye and positioned near a light source, such as a light-emitting-diode (904), laser, etc. The axis of tube member (905) is parallel to the axis of the ampoule tube (602T). Prior to actuation of the dispensing device the user aligns his eye sight with the proximal opening of the tube such that the LED light (or other light source) at the distal end of the tube is visible. In this way the device is brought to an alignment with the optical axis (906) of the eye (920) or the center of the pupil (922). The dispensing nozzle is positioned in a predetermined offset ("offset") relative to the optical axis of the tube; thus, when the device is actuated a stream of droplets or continuous stream of fluid (607) will reach the surface of the eye and will deposit at the above mentioned offset (offset) from the pupil (922). In one embodiment the offset is about, e.g., 3-10 mm.

In some embodiment the length of optical tube (905) is, e.g., 20, 30, or 40 mm, while its internal diameter ranges from, e.g., 1 to 5 mm. Preferably, the internal surfaces of the tube are coated with optically-black non-reflective coating.

In other alternative embodiments, the light source may instead be used as a fixation device to ensure delivery of the stream of fluid (607) to the proper portion of the eye. Rather than the patient aligning the optical axis of the tube with the optical axis of their eye, the light can instead be directed onto the eye by someone other than the patient, e.g., physician, nurse, family member, etc., such that the light source functions as an aiming or guiding device for directing the stream of fluid (607) onto the eye surface.

The dispensing assembly is seated or assembled on a printed circuit board (902) which includes a battery (903) and a pulse generator circuit.

Following the alignment of dispensing device (900) with the optical axis of eye electrical switch (909) is then activated by pressing on electrical switch (909). Arrow (910) illustrates the actuating vector. Electrical switch (909) further includes a linkage (908) which presses on a pedestal (802) to open the valve of the ampoule (602) as described in relation to FIG. 8A. Thus in the present invention the dispensing nozzle is normally closed but it is open momentarily during actuation of device (900).

Figure 10:
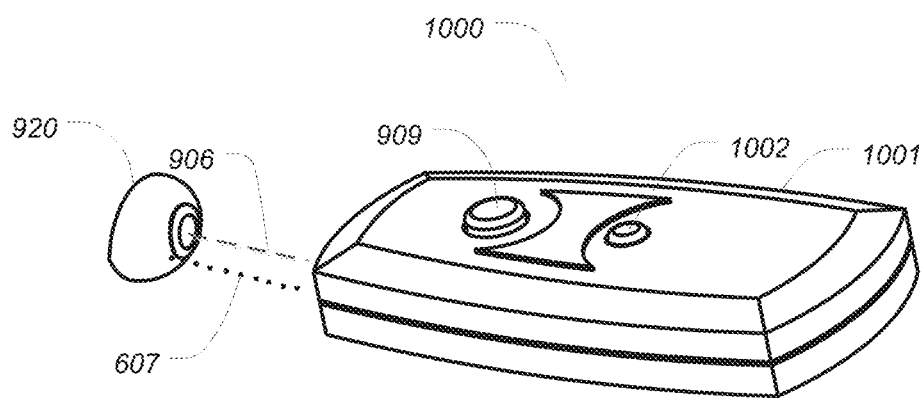
FIGS. 10 and 10A illustrate isometric views of the enclosure of the piezoelectric actuator described certain embodiments of the present invention.
Figure 10A:
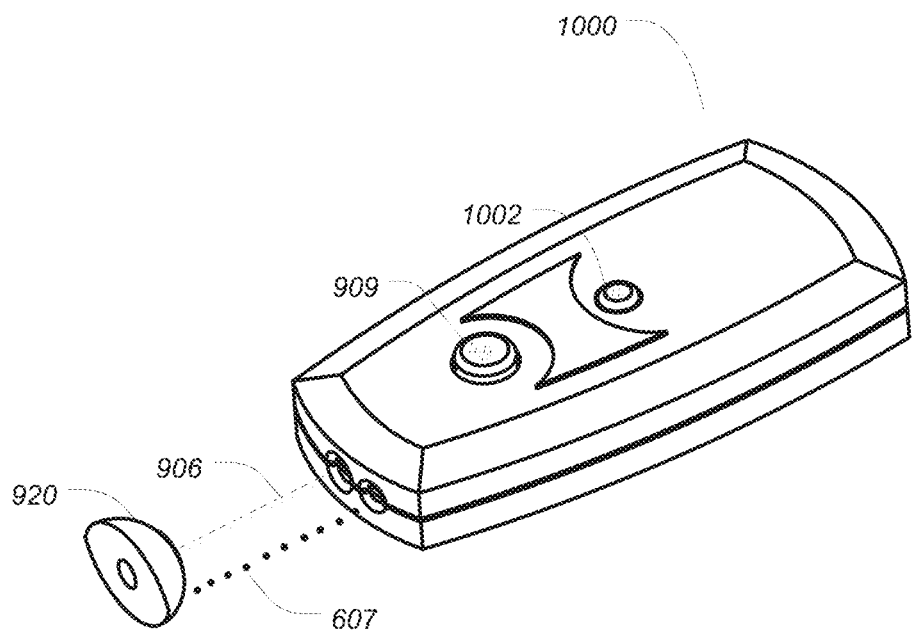

FIGS. 10 and 10A illustrate the enclosure of the dispensing device (1000) which includes the dispensing assembly. Device (1000) is aligned with the eye (920) using the optical tube as describe earlier. Device (1000) includes two electrical switches, the first switch (1002) activates the LED light, laser, etc., as described in FIG. 9 and the second switch (909) activates the dispenser once the device is aligned to the eye (920). In use device (900) is held between the thumb and the middle finger such that LED switch (1002) is pressed and turned on by the middle finger during alignment. Once the device is aligned with the eye, switch (909) is pressed by the index finger to activate the device. Droplets or stream of fluid (607) emit from the device on to the surface of the eye (920).

Figure 11:
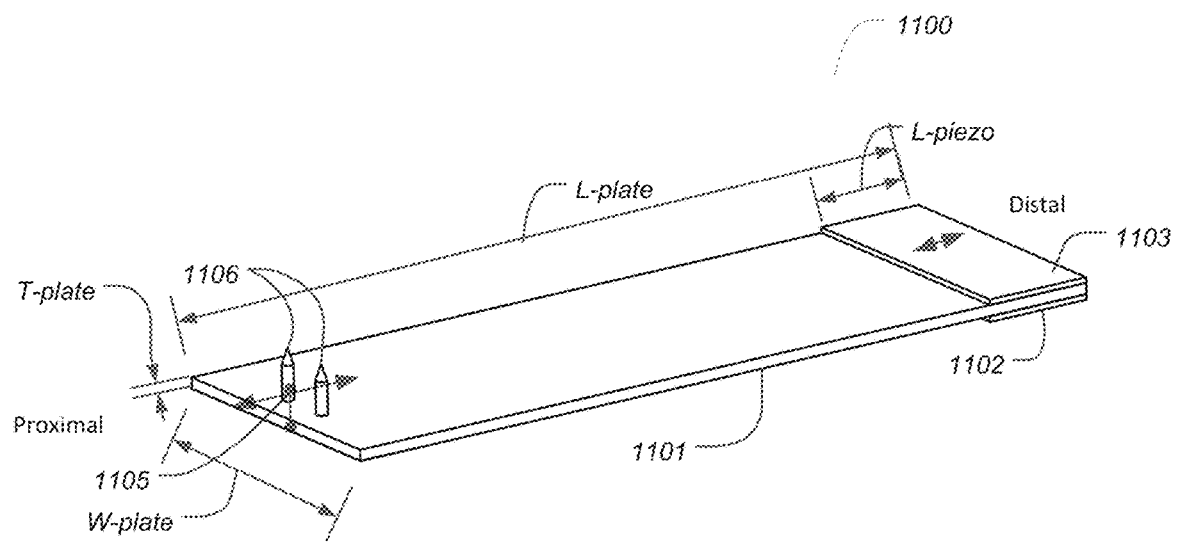
FIG. 11 illustrates a transducer plate in accordance with certain alternative embodiments of the present invention.

FIG. 11 illustrates an alternative preferred embodiment which uses piezoelectric transducer configured to oscillate a disposable drug ampoule to dispense droplets or stream of fluid along the corneal surface of the eye as will explain further below and herein. As illustrated, transducer (1100) comprising of a flat aluminum substrate plate (1101) having a length (L-plate), a width (W-plate) and a thickness (T-plate). A pair of piezoceramic plates (1102) and (1103) are structurally attached to the lower and the upper surfaces of the substrate plate (1101), preferably in close proximity to the distal end of the substrate plate (1101). Importantly, the two piezoceramic plates will have the same polarity orientation and electrical connection such that the two piezoelectric plates will expand and contract at the same directions simultaneously and without a phase shift therebetween. In this way a uniform longitudinal stress is developed in the distal end of substrate plate (1101) under the piezoceramic plate. The piezoceramic plates are connected to a pulse generator that operates at a frequency that is equal to resonance longitudinal frequency of the aluminum plate (1101). As a result the stress propagates back and forth along the plate and the plate vibrates at high amplitude expanding and contracting its length (L-plate) as indicated by the arrow (1105). Transducer plate (1101) further include two dowel pins (1106) which are integrally connected to transducer plate (1101) near the proximal end and are vibrating with the plate. In the preferred embodiment the length (L-plate) of the aluminum substrate plate is, e.g., 75 mm, its width (W-plate) is, e.g., 25 mm, and its thickness (T-plate) is, e.g., 1 mm. Other dimensions may be selected as well as other materials including, for example steel, stainless-steel and borosilicate glass, etc.

The natural or resonance longitudinal frequency of transducer plate may be calculated by the following formula below:

$$f = \frac{\lambda(i)}{2*\pi*L}\sqrt{\left(\frac{E}{\mu}\right)} \quad (3)$$

$\lambda(i) = i \cdot \pi$ (where $i = 1, 2, 3 \ldots$)
$E = 60$ GPa (module elasticity of Aluminum)
$\mu = 2700$ kg/m$^3$ (density of Aluminum)
L-plate = 75 mm (length of the plate)

It can be seen that the first natural frequency of the aluminum plate (i=1) is 31,430 Hz; the second natural frequency (i=2) is 62,850 Hz; the third natural frequency (i=3) is 94,280 Hz, etc.

Preferably the operating frequency will be the first or second natural frequency 31,430 Hz, although other natural frequencies may be selected. Advantageously, lower frequencies reduce the impact force of the droplets on the ocular surface of the eye.

Figure 11A:
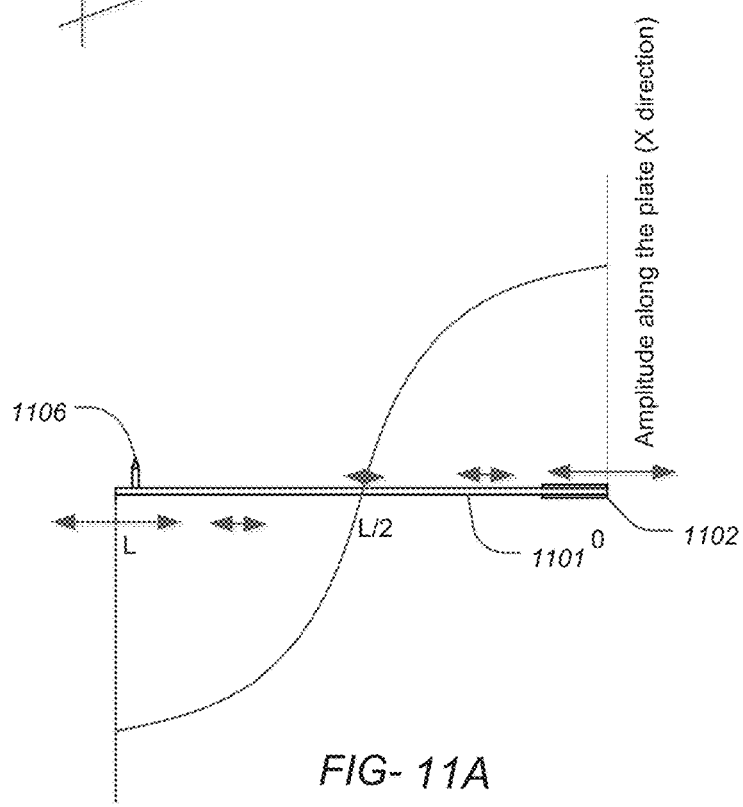
FIG. 11A illustrates a graph showing the amplitude of oscillation of the transducer plate in relation to its length.

FIG. 11A illustrates the vibration amplitude (Y axis) relative to the length of the plate (X-axis). The vibration mode shape may be calculated according to the following equation. The Y longitudinal displacement at location x along the length of the aluminum plate may be calculated by the following:

$$Y(x) = \cos\frac{i*\pi*x}{L} \quad (4)$$

where i=1, 2, 3, . . . .

It can be seen that the longitudinal displacement has a cosines profile wherein the maximum value is at the proximal and distal edges of the plate while the minimal value amplitude at the center of the plate x=Y/2=37.5 mm. This indicates that at the first longitudinal natural frequency the middle of the plate (x=37.5 mm) does not vibrate, or practically has very small vibration amplitude. Preferably the aluminum plate will be supported at or near the center such that the support minimally interferes with the vibration. In the preferred embodiment the support is made of soft elastomeric material such as silicon rubber, EPDM or the like preferably with modulus of elasticity of about, e.g., 0.3, 0.4, 0.5 GPa.

Transducer (1100) may be used to oscillate an ampoule as will explain further below. Preferably the attachment of the ampoule will be near the proximal end of the plate whereat the amplitude has a maximum value. The natural frequency of the plate is a function of its length and material properties of the plate but is nearly independent of the load, namely the weight of the ampoule, thus various sizes and types of ampoules may be used with the same transducer. Transducers with shorter or longer plates may also be selected however generally the length of the plate (L-plate) is between, e.g., 10 mm and 200 mm, and the resonance frequency is generally lower than, e.g., 500 KHz.

In one embodiment the length of piezoceramic plates (1103) and (1102) (L-Piezo) is, e.g., 10 mm. In one embodiment the length piezoceramic plate (1103) is greater than the length of piezoceramic plate (1102). In one embodiment length (L-Piezo) of piezoelectric plate (1102) may be, e.g., 20, 30, 50, or 80%, longer than piezoelectric plate (1103). In such case substrate plate (1101) will have a vibration mode which comprises of a superposition of bending mode and longitudinal mode.

In one embodiment the piezoceramic plates (1103) and (1102) are made of soft piezoceramic material such as APC 850 or APC 855 manufactured by American Piezo Corporation (APC) Mill Hall, Pa. USA.

FIG. 12 illustrates dispensing device (1200) in accordance to one embodiment of the present invention which utilize a disposable ampoule and reusable transducer. Device (1200) includes transducer plate (1100) as described in relation to FIG. 11. Dispensing device (1200) further includes a disposable ampoule (602) as described in relation to FIG. 8. Ampoule (602) includes a mounting section with two pilot holes (1207) located proximal to the aperture plate (605). As illustrated, ampoule (602) is attached to transducer (1100) by inserting the two pilot holes (1207) into of two dowel pins (1106). In this way the ampoule is locked by the interference fit between the holes (1207) and the dowel pins (1106). As explained earlier in relation to FIG. 11 the proximal end of longitudinal transducer plate and the dowel pins oscillates at high amplitude thereby oscillations are transmitted to the body of the ampoule and to the aperture plate (605) which in turn ejects stream of droplet (1210).

In one embodiment the longitudinal transducer plate includes a third piezoceramic plate (1102) which is configured to produces a bending mode at the proximal end of the plate. Such a bending mode disperses the drops (1210) and reduces the droplets impact for on the eye. In one embodiment the length piezoceramic plates (1103) is, e.g., 20 mm, and the length of piezoceramic plate (1102) is, e.g., 10 mm, which in turn produces a superposition of bending and longitudinal modes which in turn causes a dispersion of droplets (1210).

FIG. 13 illustrates dispensing device (1300) in accordance to some embodiments of the invention that utilize disposable ampoules and reusable transducer. Device (1300) includes a mechanical oscillator or transducer (1301) driven by multilayer piezoelectric stacks (1306). Mechanical oscillator (1301) comprising a body which includes two parallel plates which are connected by a flexible linkages. As illustrated, the first parallel plate (1302) is stationary and the second plate (1303) is vibrateable. The two plates are connected by flexible linkages (1304) and (1305). Piezoceramic stack (1306) is positioned between the end of the vibrateable plate (1303) and a stationary or fixed support (1308). Piezoceramic stack extends and contracts against the end of plate (1303) in the X direction as indicated by the arrows (1306) thereby transmitting vibration amplitude to the plate (1303) in the X direction as indicated by the arrows (1307). It can be seen however, that flexible link (1304) is connected to the vibrateable plate (1303) in a slanted angle (1309) relative to the stationary plate (1302). In this way the vibration amplitude and velocity transmitted to plate (1303) has an X component and a Y component. The first X component is in the displacement direction of the piezoceramic stack and the second Y component is perpendicular to the direction of the piezoceramic stack.

In one embodiment piezoceramic stack (1306) manufactured by NEC part No. AE203D04F is sold by THORLABS INC. Newton, N.J. USA. In one embodiment the angle (1309) of the flexible linkage (1304) is, e.g., 150 deg. In some embodiment mechanical oscillator (1301) is made of extruded material such as aluminum type 2024 or thermoplastics such as Delrin™.

Figure 12:
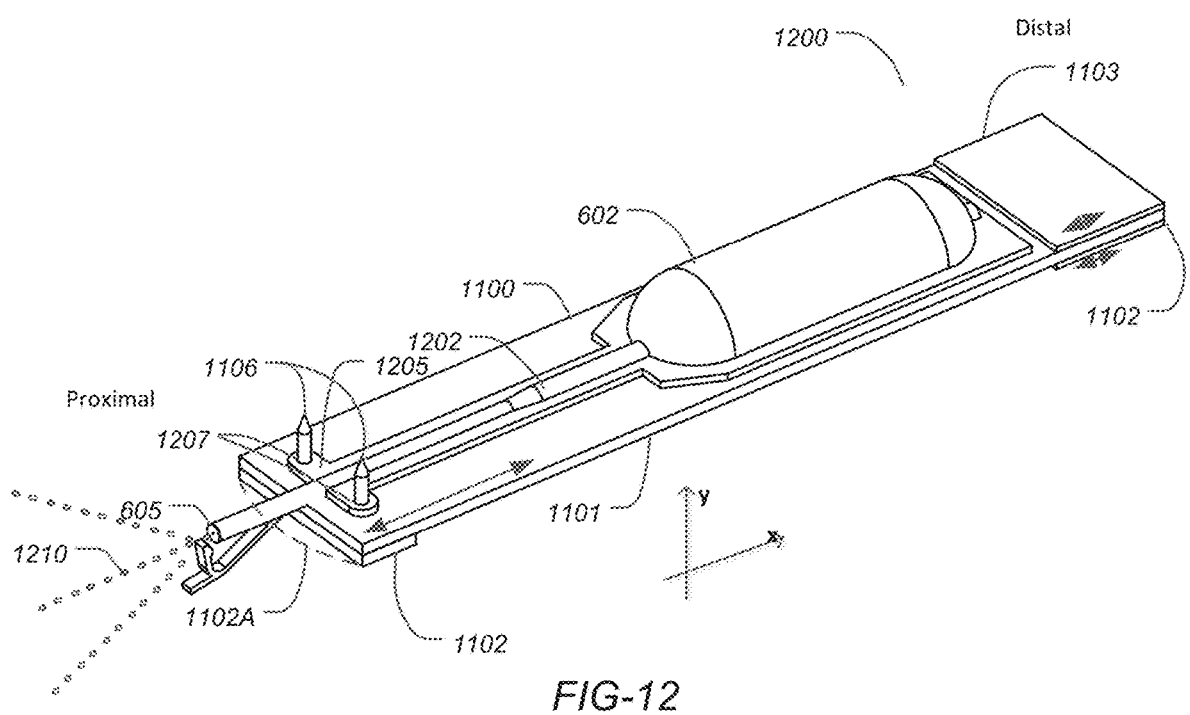
FIG. 12 illustrates the assembly of the transducer plate with an ampoule in accordance to certain embodiments of the invention.
Figure 13:
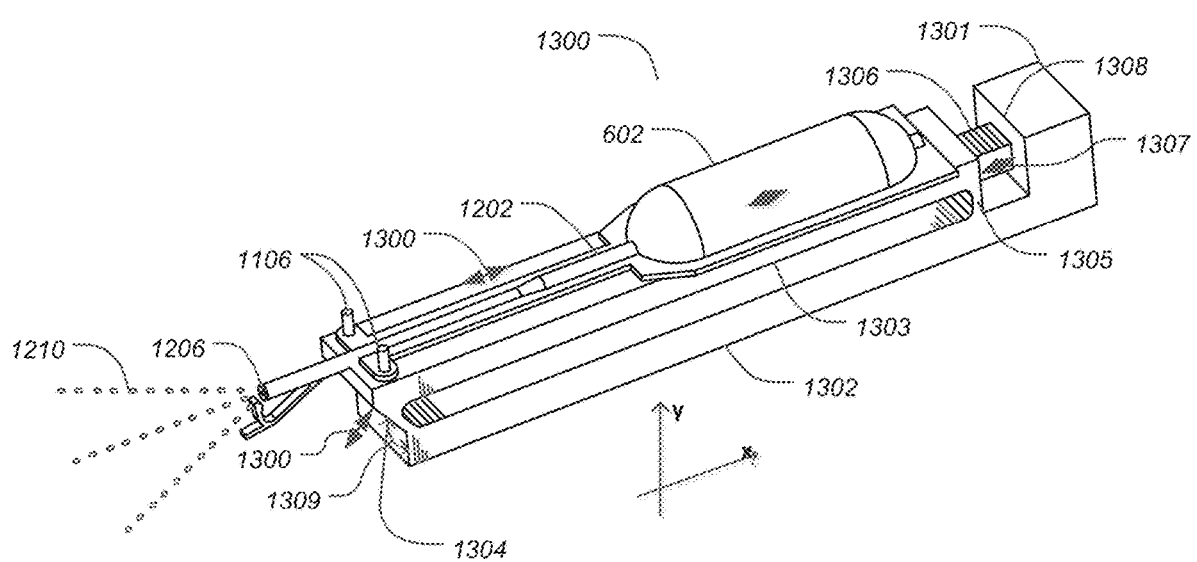
FIG. 13 illustrates the assembly of the mechanical oscillator plate with an ampoule in accordance to certain embodiments of the invention.
Figure 14:
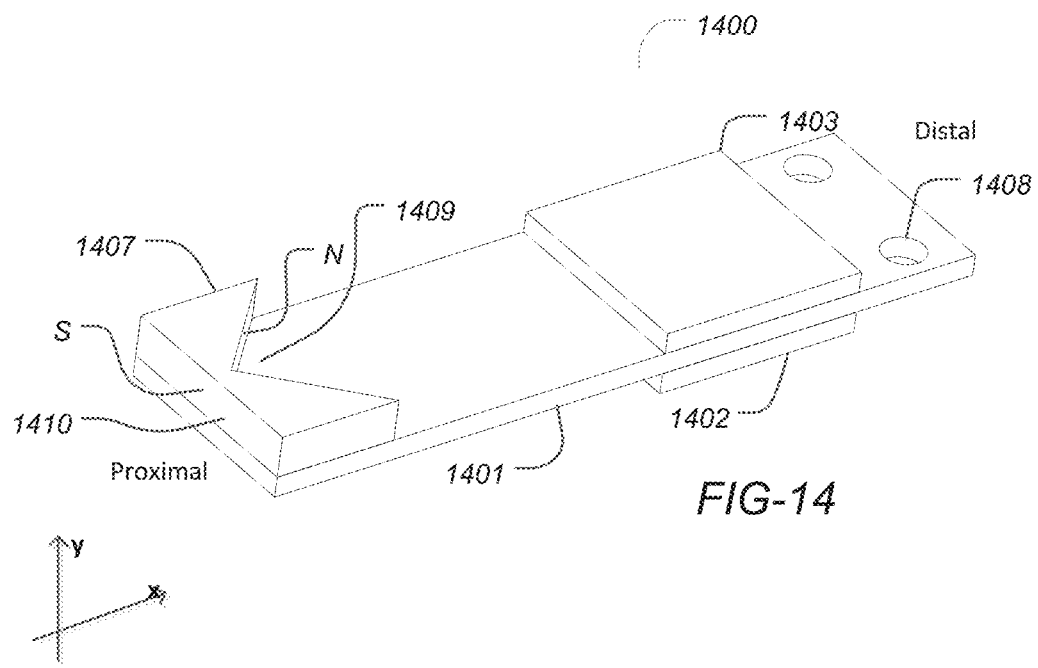
FIG. 14 illustrates a piezoelectric transducer configured to oscillate a disposable drug ampoule.
Figure 15:
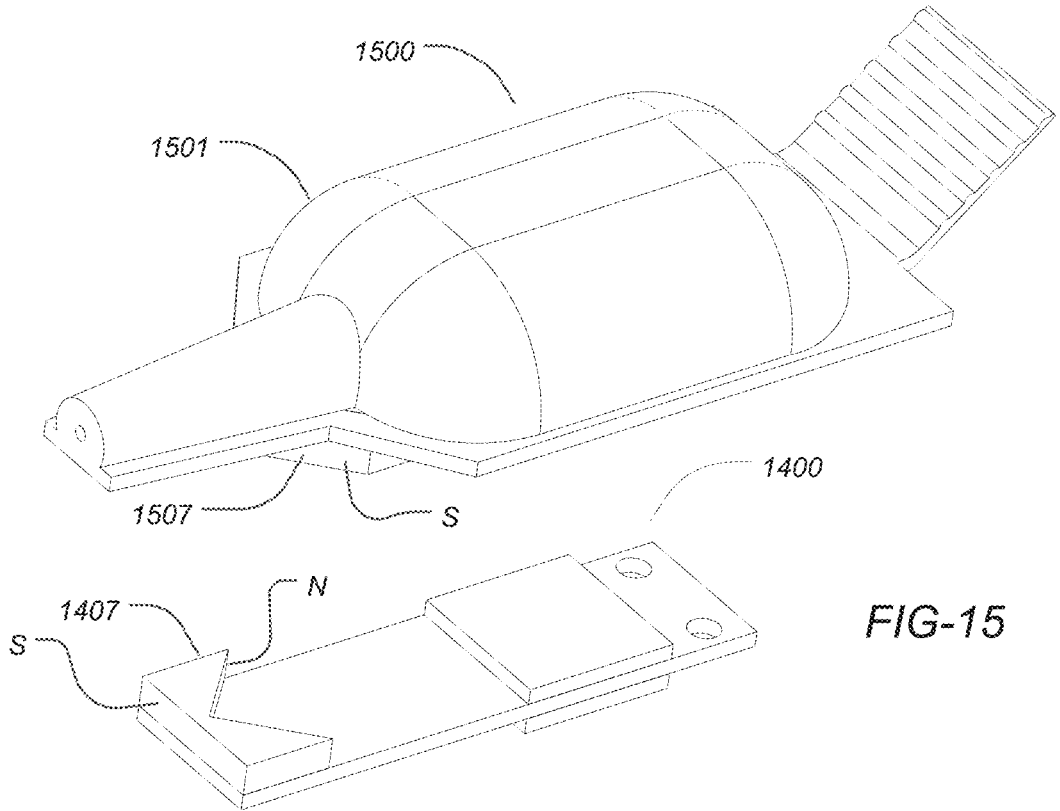
FIG. 15 illustrates an exploded view showing a transducer and ampoule from a side view.
Figure 16:
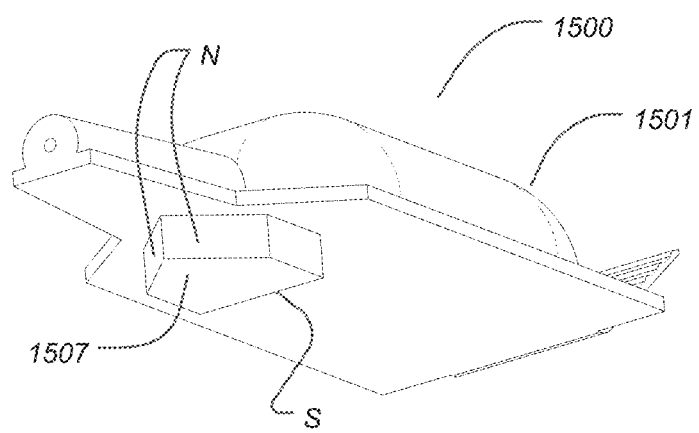
FIG. 16 illustrates an exploded view showing a transducer and ampoule from a bottom view.
Figure 16:
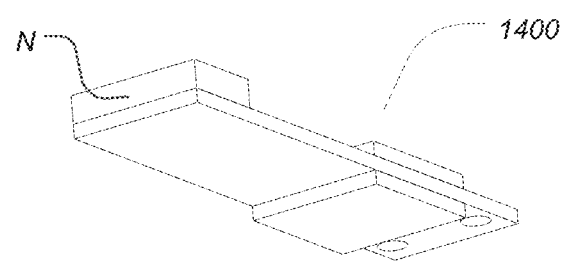
Figure 17:
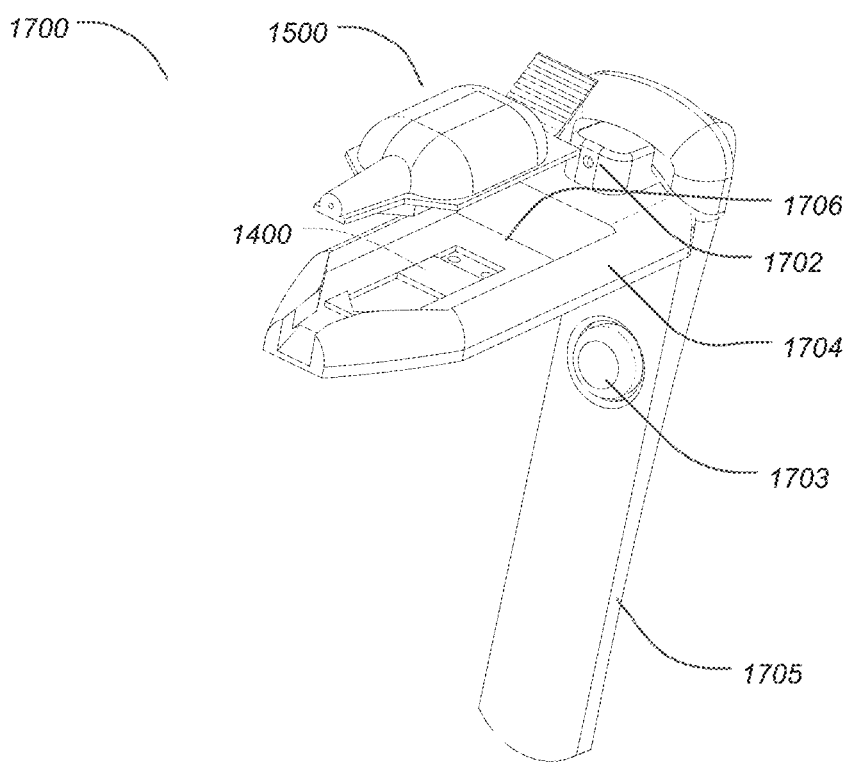
FIG. 17 illustrates an exploded view of the dispensing assembly which includes an ampoule and a transducer within an housing.
Figure 18:
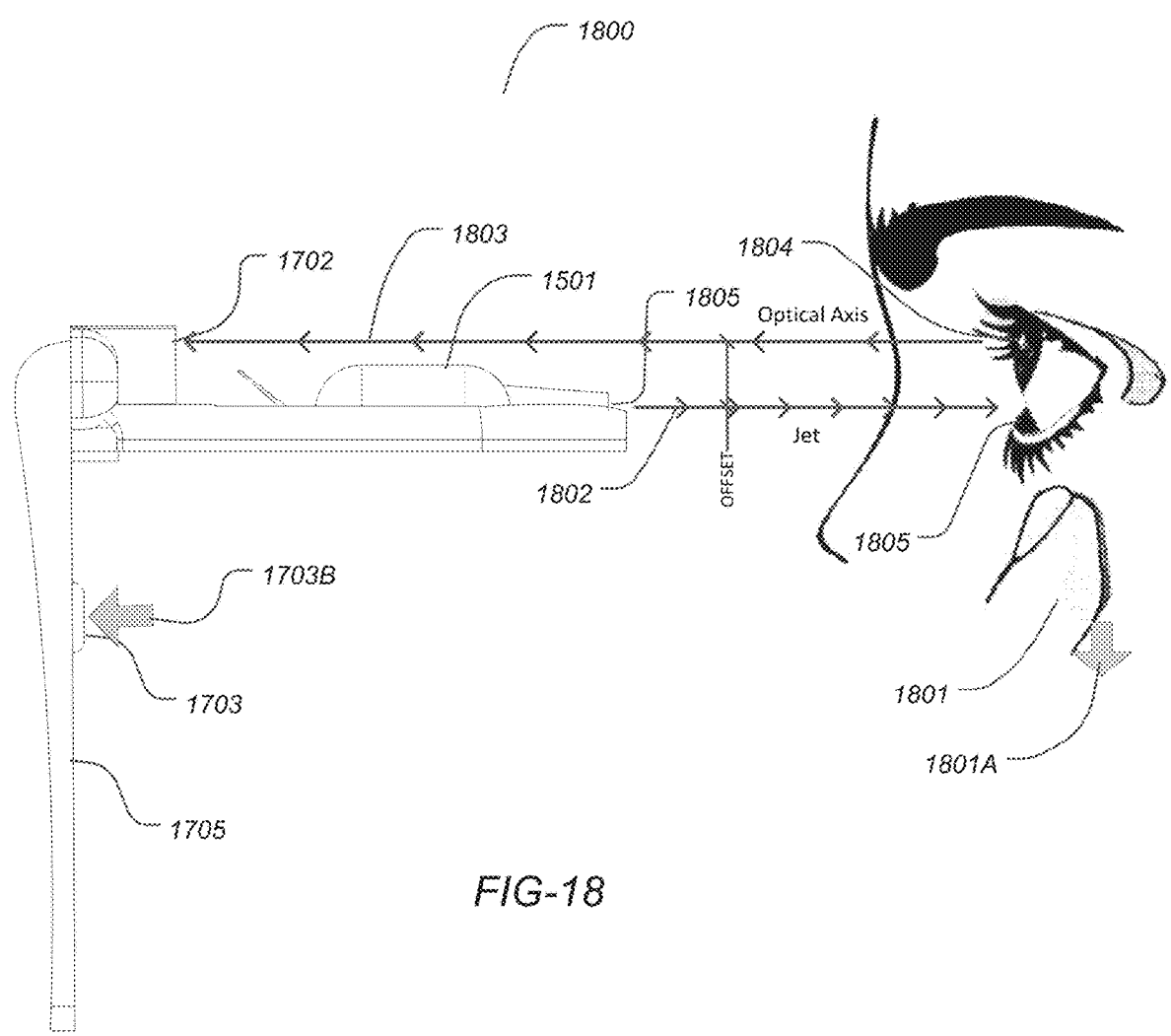
FIG. 18 illustrates how the device may be aligned to the eye prior to and during use.
Figure 19:
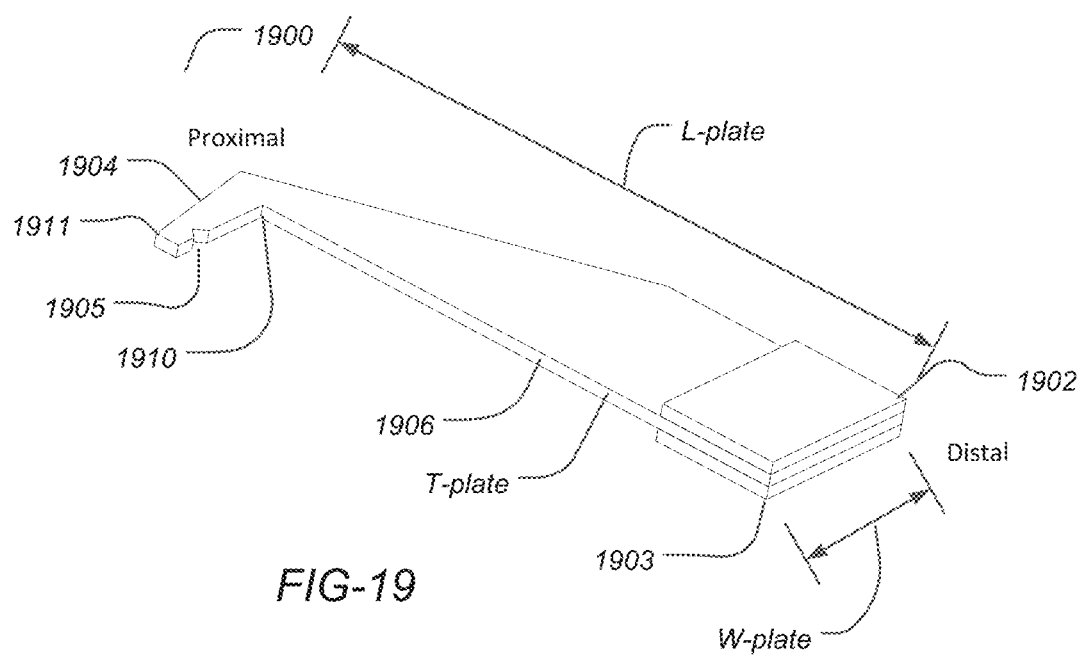
FIGS. 19 and 19A illustrate perspective and frontal views of an alternative transducer embodiment configured to produce high oscillation amplitudes.
Figure 19A:
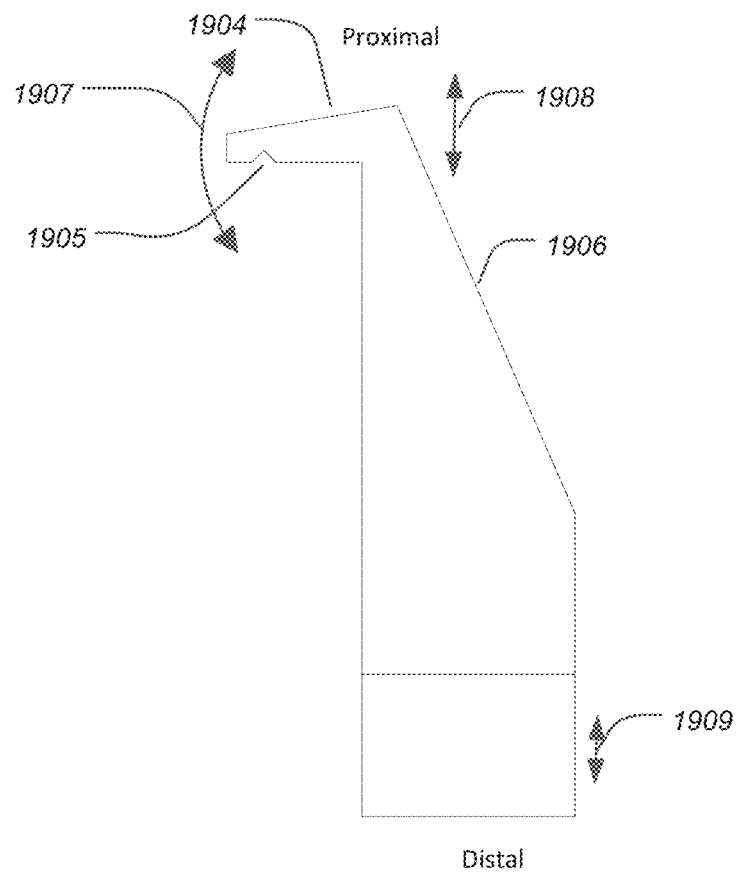

Dispensing device (1300) further includes a disposable ampoule (602) and two dowel pin similar to the one discussed earlier in relation to FIG. 12. Oscillation of the disposable ampoule in the X and Y direction produces dispersion of droplets in a fan shape or a conical shape, thus reducing the impact of the droplet on the corneal surface.

Advantageously, operation of device (1300) is not dependent of the natural frequency of the oscillator (1301). Device (1300) will operate at subsonic frequencies which further reduces the impact force of the drop on the eye. Preferably the electrical input signal to the piezoceramic stack (1306) is a square wave with a rapid rise and fall. Preferably operating frequency is below, e.g., 10 kHz, and more preferably at about, e.g., 4 kHz. Lower frequencies further reduce the impact force of the droplets against the surface of the eye.

FIG. 14 illustrates a piezoelectric transducer configured to oscillate a disposable drug ampoule to dispense collimated solid stream to the area of the inferior conjunctiva of the eye as will explain further below and herein. As illustrated, transducer (1400) may be comprised of a flat steel substrate plate (1401) having a length (L-plate), a width (W-plate) and a thickness (T-plate), although other embodiments may utilize other materials and dimensions. A pair of piezoceramic plates (1402) and (1403) are structurally attached to the lower and the upper surfaces of the substrate plate (1401), preferably in close proximity to the distal end of the substrate plate (1401). The two piezoceramic plates will preferably have the same polarity orientation and electrical connection such that the two piezoelectric plates will expand and contract at the same directions simultaneously and without a phase shift therebetween. In this way a uniform longitudinal stress is developed in the distal end of substrate plate (1401) under the piezoceramic plates. The piezoceramic plates are connected to a pulse generator that operates at a frequency that is equal to natural longitudinal frequency of the substrate plate (1401). As a result the stress propagates back and forth along the plate and the proximal end of the plate vibrates at high amplitude expanding and contracting its length (L-plate). Substrate plate (1401) may further include a magnet (1407) which serves to hold and retain the ampoule as will explain further below. The magnet is integrally connected near the proximal end of substrate plate (1401) by, e.g., a structural adhesive (such as Loctite Epoxy type E-120HP). As shown in FIG. 14 magnet (1407) has a 90 degrees V-shape profile (1409) on one side and a flat face on the opposite side. Other attachment mechanisms may also be utilized, if so desired, in other variations. Magnet (1407) is polarized along the X-axis such that the V-shape profile (1409) defines one pole of the magnet (N) and the opposite side (1410) defines the second opposite (S).

Referring now to FIG. 15 and FIG. 16 which illustrate two exploded views showing transducer (1400) and ampoule (1500) from a side view and a bottom view respectively. As described earlier transducer (1400) includes a magnet (1407) which has a recessed V-shaped profile. Ampoule (1501) includes a magnet (1507) that is integrally attached to its body. Magnet (1507) has an arrow-shape profile. When the user places the ampoule on transducer (1400) the magnetic attraction pulls the ampoule and positions it tightly against the transducer such that the arrow-shape magnet (1507) engages with the V-shape magnet. In this way the transducer oscillations are effectively transmitted to the ampoule which consequently causes ejection of fluid from the ampoule. In the preferred embodiment the two magnets are made of Niobium, a rare earth metal. Other rare earth magnet may be use such as samarium cobalt or simple magnetized ferromagnetic material such as iron or steel. Magnet (1507) may be replaced by a ferromagnetic material that is not magnetized. When two magnets are used the polarity of the arrow-shape on one magnet and the V-shape on the second magnet are opposite. In other embodiments, the magnets may be shaped in other configurations aside from the V-shape so long as the complementary portions are keyed so as to be readily and easily aligned in a consistent manner.

With respect to the amount of magnetic force, the embodiment shown may generally utilize at least, e.g., 0.5 N, of magnetic force between the magnets and in other embodiments, at least, e.g., 25 N, of magnetic force to securely maintain the ampoule position relative to the transducer and housing during transducer vibration.

FIG. 17 illustrates an exploded view of dispensing assembly (1700) which includes an ampoule (1400) and a transducer (1500) within housing (1704). Housing (1704) has a cradle-shape cavity (1706) for placing the ampoule within. Once the ampoule is placed within the cavity the magnetic attraction pulls the ampoule and locks it to the transducer as described earlier.

Dispensing assembly (1700) further includes a handle (1705) and an activation switch (1703). Dispensing assembly (1700) further includes an optical mechanism to align the dispensing device to the inferior conjunctiva of the eye prior to actuation. The alignment mechanism includes a small diameter bore (1702) having a predetermined diameter and depth. A light source (not shown) may be positioned inside the distal end of the bore (1702) while the proximal opening of the bore is generally oriented toward the eye.

Referring now to FIG. 18 which illustrates how the device is aligned to the eye. Prior to actuation of the dispensing device the user aligns the device such that the light source at the distal end of the bore (1702) is visible as illustrated by line (1803). In this way the bore (1702) and the device itself are brought to an alignment with the optical axis of the eye or the center of the pupil (1804). The dispensing nozzle (1805) is automatically positioned in a predetermined vertical offset (offset) below the optical axis (1803) of the eye. Thus, when the device is actuated, a stream of fluid will reach the area below the pupil and will deposit at the above mentioned (offset). In the preferred embodiment the offset is about, e.g., 8 mm, below the pupil will dispense fluid onto the area of the inferior conjunctiva (1806). Conveniently, the user may hold the handle (1705) of the device in one hand while optionally pulling down the area below the eyelid (1801) and pull down slightly as indicated by arrow (1801A) and pressing the activation switch (1703B) to ensure a clear path of the jet (1802).

FIG. 19 and FIG. 19A illustrate an isometric and frontal views of alternative transducer embodiment configured to produce high oscillation amplitude. Transducer (1900) is configured to oscillate a disposable drug ampoule to dispense droplets or stream of fluid along the corneal surface or the lower conjunctiva. As illustrated, transducer (1900) is comprised of a flat steel substrate plate (1906) having a length (L-plate), a width (W-plate) and a thickness (T-plate). A pair of piezoceramic plates (1902) and (1903) are structurally attached to the lower and the upper surfaces of the flat steel substrate plate (1906), preferably in close proximity to the distal end of the flat steel substrate plate (1906). The two piezoceramic plates will have the same polarity orientation and electrical connection such that the two piezoelectric plates will expand and contract at the same directions simultaneously and without a phase shift therebetween. In this way a uniform longitudinal stress is developed in the distal end of the flat steel substrate plate (1906) under the piezoceramic plate. The piezoceramic plates are connected to a pulse or signal generator that operates at a frequency that is equal to natural longitudinal frequency of the flat steel substrate plate (1906). As a result the stress propagates back and forth along the flat steel substrate plate and the flat steel substrate plate vibrates at high amplitude expanding and contracting along its length (L-plate).

It can be seen that flat steel substrate plate (1906) is relatively wider near the piezoceramic elements and is gradually tapering along the length (L-Plate) of the flat steel substrate plate (1906). In this way the stress distribution is gradually increased toward the distal end. As illustrated oscillation amplitude (1908) at the distal end of the transducer are relatively higher than the oscillation amplitude (1909) near the proximal end where the piezoceramic elements are located. It can be seen that flat steel substrate plate (1906) further includes an extension (1904) that extends in a perpendicular direction relative to the length of the flat steel substrate plate (1906). Extension (1904) functions as a cantilever beam that is attached to the flat steel substrate plate (1906) at its distal end (1910) and is free to oscillate at the second end (1911) of the extension (1904). The free end (1911) oscillates at a relatively higher amplitude (1907) when compared to the oscillation of the transducer (1902) and (1903). Extension (1904) may further include a groove or notch, e.g., V-groove (1905), defined along a proximal edge of the extension (1904) that may be used to secure the ampoule to the transducer. Preferably the natural frequency of the cantilever beam (1904) is equal to the natural frequency of the transducer (1900).

The applications of the disclosed invention discussed above are not limited to the embodiments described, but may include any number of other applications and uses. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A handheld device for emitting a fluid onto a surface of an eye, the device comprising:
   a piezoelectric actuator configured to vibrate at a selected frequency;
   an ampoule containing:
     a fluid reservoir containing the fluid to be dispensed; and
     an aperture; and
   an attachment mechanism configured to removably couple the ampoule into vibrational conduction with the piezoelectric actuator so that the piezoelectric actuator touches an external surface of the ampoule, wherein the attachment mechanism comprises a clamp, wherein the clamp is a C-clamp;
   wherein;
   the ampoule is aligned in a predetermined orientation relative to the piezoelectric actuator such that the fluid is emitted through the aperture when the piezoelectric actuator exerts acoustic pulses on the external surface of the ampoule; and
   fluid emitted through the aperture can be directed onto the surface of the eye.

2. The device of claim 1 wherein the fluid reservoir comprises an ophthalmic composition.

3. The device of claim 1 wherein the fluid reservoir has a volume of about 3000 µL.

4. The device of claim 1 further comprising a shut-off valve which is configured to seal the aperture.

5. The device of claim 1 wherein the fluid is emitted from the device as a collimated stream.

6. The device of claim 1 wherein the fluid reservoir comprises a blister and an elongated conduit extending from the blister to the aperture.

7. The device of claim 1 wherein the ampoule is made of a thermoplastic polymer.

8. The device of claim 1 wherein the aperture of the ampoule comprises a single aperture.

* * * * *